US008633308B2

(12) United States Patent
Schang et al.

(10) Patent No.: US 8,633,308 B2
(45) Date of Patent: Jan. 21, 2014

(54) COMPOUNDS FOR PREVENTING OR TREATING VIRAL INFECTIONS AND METHODS OF USE THEREOF

(75) Inventors: Luis M. Schang, Edmonton (CA); Mireilli R. St. Vincent, Edmonton (CA); Alexey V. Ustinov, Moscow (RU)

(73) Assignee: The Governors of The University of Alberta, Edmonton, Alberta (CA)

( * ) Notice: Subject to any disclaimer, the term of this patent is extended or adjusted under 35 U.S.C. 154(b) by 1014 days.

(21) Appl. No.: 12/038,345

(22) Filed: Feb. 27, 2008

(65) Prior Publication Data

US 2012/0135954 A1 May 31, 2012

Related U.S. Application Data

(60) Provisional application No. 60/891,954, filed on Feb. 28, 2007.

(51) Int. Cl.
*A61K 31/7072* (2006.01)
*C07H 19/09* (2006.01)

(52) U.S. Cl.
CPC ............ *A61K 31/7072* (2013.01); *C07H 19/09* (2013.01)
USPC .................................... 536/28.53; 536/28.54

(58) Field of Classification Search
None
See application file for complete search history.

(56) References Cited

U.S. PATENT DOCUMENTS

| | | | |
|---|---|---|---|
| 5,534,554 A | | 7/1996 | Katz et al. |
| 5,658,956 A | * | 8/1997 | Martin et al. ................. 514/724 |

FOREIGN PATENT DOCUMENTS

| | | |
|---|---|---|
| CA | 2375385 A1 | 12/2000 |
| CA | 2252813 | 6/2007 |
| WO | 0183501 | 8/2001 |
| WO | 0232920 | 4/2002 |
| WO | 03053360 | 7/2003 |

OTHER PUBLICATIONS

"Definition of derivertive", retrieved from Merriam-Webster online dictionary <<http://www.merriamwebster.com/dictionary/derivative>> on Apr. 6, 2011, 2 pages.*
Robins et al., J. Med. Chem. 1991, 34, 2275-2280.*
Morin et al. J. Med. Chem. 1997, 40, 2184-2190.*
Lautens et al., Angew. Chem. Int. Ed. 2000, 39, No. 6, 1045-1046.*
Ashida et al., Antiviral Research, 1997, 35, 167-175.*
Colpitts et al., "5-(Perylen-3-yl)Ethynyl-arabino-Uridine (aUY11), an Arabino-Based Rigid Amphipathic Fusion Inhibitor, Targets Virion Envelope Lipids to Inhibit Fusion of Influenza Virus, Hepatitis C Virus, and Other Enveloped Viruses" Journal of Virology (2013) vol. 87 No. 7 pp. 3640-3654.*
St. Vincent et al., "Rigid amphipathic fusion inhibitors, small molecule antiviral compounds against enveloped viruses" PNAS (2010) vol. 107 No. 40 pp. 17339-17344.*
Flasche et al.,"Lipophilic Nucleosides by Sonoghashira Coupling" Synthesis, Georg Thieme Verlag, Stuttgart, DE, No. 14, Aug. 25, 2004, pp. 2335-2341. XP002386480.
McGuigan et al., "Novel Aryl Substituted Bicyclic Furo Nucleosides As Extremely Potent and Selective Anti-VZV Agents" Nucleosides, Nucleotides & Nucleic Acids, 20(4-7), 287-296 (2001), XP009116423.
Rahim et al., 5-Alkynyl pyrimidine nucleosides as potent selective inhibitors of varicella-zoster virus, Antivir. Chem, Chemother. 1992, 3(5):293-297.
Rai et al., "Design and Studies of Novel 5-Substituted Alkynylpyrimidine Nucleosides as Potent Inhibitors of Mycobacteria" J Med Chem, 2005, 48, 7012-7017, XP002526901.
Rai et al., Inhibition of *Mycobacterium tuberculosis, Mycobacterium bovis*, and *Mycobacterium avium* by Novel Dideoxy Nucleosides, J Med Chem, 2007, 50, 4766-4774.
Reefschlager et al., "Antiherpes activity of (E)-5-(2-bromovinyl)- and 5-vinyl-1-β-D-arabinofuranosyiuracil and some other 5-substituted uracil arabinosyl nucleosides in two different cell lines" Antiviral Res, 3 (1983) 175-187.
Sharma et al., "Acetylenic Nucleosides. 3, Synthesis and Biological Activities of Some 5-Ethynylpyrimidine Nucleosides", J Med Chem 1984, 27(3):410-412. XP-002526904.
Korshun et al., Aikynylated Nucleosides and Their Analogues. I. Methods of Synthesis, Russ J Bioorg Chem, 1997, 23(5);324-387.
PCT/IB2008/001625, Notification of Transmittal of the International Search Report and the Written Opinion of the International Searching Authority, or the Declaration, European Patent Office, dated May 19, 2009.
PCT/IB2008/001625, Notification of Transmittal of the International Search Report and the Written Opinion of the International Searching Authority, or the Declaration, Canadian Patent Office, dated Apr. 14, 2009.
Shinji Harada; "The broad anti-viral agent glycyrrhizin directly modulates the fluidity of plasma membrane and HIV-1 envelope"; Biochemical Society; (2005); pp. 191-199; vol. 392; Great Britain.
Michael L.Greenberg, Nick Cammack; "Resistance to enfuvirtide, the first HIV fusion inhibitor"; Journal of Antimicrobial Chemotherapy; (2004); pp. 333-340; vol. 54 No. 2; Great Britain.
A.A. Pchelintseva, M.V. Skorobogatyj, A.L. Petrunina, V. L. Andronova, G. A. Galegov, I. V. Astakhova, A. V. Ustinov, A. D. Malakhov, Vladimir A. Korshun; "Synthesis and Evaluation of Anti-HSV Activity of New 5-Alkynyl-2'-Deoxyuridines"; Nucleosides, Nucleotides, and Nucleic Acids, Taylor & Frances, Inc.; (2005); pp. 923-926; vol. 24 (5-7).
V. A. Korshun, E. V. Manasova, K. V. Balakin, A. D. Malakhow, A. V. Perepelov, T. A. Sokolova, Yu. A. Berlin; "New Fluorescent Nucleoside Derivatives—5-Alkynylated 2'-Deoxyuridines"; Nucleosides & Nucleotides; Marcel Dekker, Inc.; (1998); pp. 1809-1812; vol. 17 (9-11).

(Continued)

*Primary Examiner* — Eric S Olson
(74) *Attorney, Agent, or Firm* — Gardner, Groff, Greenwald & Villanueva, P.C.

(57) ABSTRACT

Described herein are compounds and methods that prevent the viral infection of cells. The compounds and methods described herein minimize viral resistance and maximize the number of targeted viruses. Additionally, the compounds and methods minimize the toxicity toward uninfected cells.

5 Claims, 19 Drawing Sheets

(56) References Cited

OTHER PUBLICATIONS

Mikhail V. Skorobogatyi, Alexei V. Ustinov, Irina A. Stepanova, Anna A. Pchelintseva, Anna L. Petrunina, Valeriya L. Andronova, Georgi A. Galegov, Andrei D. Malakhov, Vladimir A. Korshun; 5-Arylethynyl-2'-deoxyuridines, compounds active against HSV-1' Organic & Biomolecular Chemistry, The Royal Society of Chemistry; (2006); pp. 1091-1096; vol. 4.
V. L. Andronova, M. V. Skorobogatyi, E. V. Manasova, Yu. A. Berlin, V. A. Korshun, G. A. Galegov; "Antiviral Activity of Some 2'-Deoxyuridine 5-Arylethynyl Derivatiaves"; Russian Journal of Bioorganic Chemisty; (2003); pp. 262-266; vol. 29 No. 3; Translated from Bioorganicheskaya Khimiya, pp. 290-295; vol. 29, No. 3.
Shinji Harada, Kazumi Yokomizo, Kazuaki Monde, Yosuke Maeda, Keisuke Yusa; "A broad antiviral neutral glycolipid, fattiviracin FV-8, is a membrane fluidity modulator"; Cellular Microbiology; (2006); pp. 3-8.
Mikhail V. Skorobogatyi, Anna A. Pchelintseva, Anna L. Petrunina, Irina A. Stepanova, Valeriya L. Andronova, Georgi A. Galegov, Andrei D. Malakhov, and Vladimir A. Korshun; "5-Alkynyl-2'-deoxyuridines, containing bulky aryl groups: evaluation of structure-anti-HSV-1 activity relationship"; Tetrahedron (2006); pp. 1279-1287; vol. 62.
A.D. Malakhov , E.V. Malakhova, S.V. Kuznitsova, I.V. Grechishnikova, I.A. Prokhorenko, M.V. Skorobogatyi, V.A. Korshun, and Yu.A. Berlin; "Synthesis and Fluorescent Properties of 5-(1-Pyrenylethynyl)-2'-deoxyuridine-containing Oligodeoxynucleotides"; Russian Journal of Bioorganic Chemistry, vol. 26, No. 1, 2000, pp. 34-44; Translated from Bioorganicheskaya Khimiya, vol. 26, No. 1, 2000, pp. 39-50. in final form, Jul. 5, 1999.
Descamps et al. "Inhibitory Effect of E-5-(2-Bromovinyl)-l-Ip-DArabinofuranosyluracil on Herpes Simplex Virus Replication and DNA Synthesis" Journal of Virology, 1982, vol. 43, No. 1, p. 332-336.
Grignet-Debrus et al. "The role of Cellular- and producing-associated factors in the bystander effect induced by the Varicella zoster and Herpes simplex viral thymidine kinases in suicide gene therapy", Gene Therapy, vol. 7, No. 11, pp. 14566-1468, Nature America, Inc. 2000.
Grignet-Debrus et al. "Comparative in vitro and in vivo cytotoxic activity of 9 (E)-5-(2-bromovinyl)-2'-deoxyuridine (BVDU) and its arabinosyl derivative, (E)-5-(2-bromovinyl)-1-B-D-arabinofuranosyluracil (BVaraU), against tumor cells expressing either thymidine kinase" Gene Therapy, vol. 7, No. 2, pp. 215-223, Nature America, Inc. 2000.
Machida et al., "In Vitro Antiherpesviral Activity of 5-Alkyl Derivatives of 1-B-d-Arabinofuranosyluracil", Antimicrobial Agents and Chemotherapy, Aug. 1979, vol. 16, No. 2 p. 158-163, Marcel Dekker, Inc.
McGuigan et al., "Novel Aryl Substituted Bicyclic Furo Nucleosides As Extremely Potent and Selective Anti-VZV Agents", Nucleosides, Nucleotides & Nucleic Acids, 20(4-7), 287-296 (2001).
McGuigan et al., "Furano pyrimidines as novel potent and selective anti-VZV agents", Antiviral Chemistry & Chemotherapy vol. 12 pp. 77-89, International Medical Press.
Meneni et al. "5-Alkynyl-20-deoxyuridines: Chromatography-free synthesis and cytotoxicity evaluation against human breast cancer cells", Bioorganic & Medicinal Chemistry 15 (2007) 3082-3088, Elsevier Ltd.
Reefschlager et al., "Antiherpes activity of (E)-5-(2-bromovinyl)- and 5-vinyl-1-β-D-arabinofuranosyluracil and some other 5-substituted uracil arabinosyl nucleosides in two different cell lines", Antiviral Research vol. 3, Issue 3, Sep. 1983, pp. 175-187, Elsevier Science B.V.
Suzutani et al., "Efficacies of Antiherpesvirus Nucleosides against Two Strains of Herpes Simplex Virus Type 1 in Vero and Human Embryo Lung Fibroblast Cells", Antimicrobial Agents and Chemotherapy, Jul. 1988, vol. 32, No. 7, p. 1046-1052, American Society for Microbiology.
Yokota et al., "Mechanism of Selective Inhibition of Varicella Zoster Virus Replication by 1-f3-D-Arabinofuranosyl|E-5-(2-bromovinyl)uracil", Molecular Pharmacology, 36:312-316,The American Society for Pharmacology and Experimental Therapeutics.
Bouamaied et al., Synlett, 2004, (9), p. 1579-1583.
Van Draanen et al., Nucleoside & Nucleotides, 1994, vol. 13(8), p. 1679-1693.
Office Action for Japanese application No. 2009-551286 dated Mar. 12, 2013.

* cited by examiner

COMPOUNDS FOR PREVENTING OR TREATING VIRAL INFECTIONS AND METHODS OF USE THEREOF

CROSS REFERENCE TO RELATED APPLICATION

This application claims priority upon U.S. provisional application Ser. No. 60/891,954, filed Feb. 28, 2007. This application is hereby incorporated by reference in its entirety for all of its teachings.

BACKGROUND

As a result of the extensive research in the discovery of antiviral drugs, 43 antiviral drugs are currently approved worldwide for clinical use. However, most of them target the viral DNA polymerases. Such bias is likely due to the HSV-1 DNA polymerase being the first target ever identified for antiviral drugs. The second target discovered were the viral proteases, which are required for virion maturation. More recently, significant efforts have been placed in developing drugs that target other viral proteins. A major emphasis is on drugs that inhibit viral infectivity, wherein the drugs would block the very first events in the viral infection process. The first successful inhibitor of infectivity was T-20 or fuzeon, a peptidic inhibitor of the rearrangements of the HIV fusion proteins. This drug is clinically used, but only in combination therapies. Moreover, the drug has already selected for resistance. More recently, the interaction between the HIV glycoproteins and their cellular receptors or coreceptors has also been targeted (e.g., vicriviroc-SCH 417690, TAK-779, PRO-140, UK-427,857, GW873140 and AMD887, which all target the CCR5 coreceptor, or AMD3100 and AMD070, which target the CXCR4 coreceptor). However, all these inhibitors of infectivity suffer from significant drawbacks. For example, the peptide inhibitors have poor bioavailability and stability. Thus, they must be prepared shortly before use and can only be used by parental administration. The inhibitors of coreceptor binding have narrow specificities (such as only CCR5 or CXCR4-trophic viruses). Moreover, the inhibitors of receptor binding can also block the activities of important cellular receptors. Therefore, significant efforts are still invested in developing novel inhibitors of viral fusion that can overcome such limitations.

Current inhibitors of viral fusion target interactions between viral and cellular proteins. Indeed, all antiviral drugs have been traditionally developed to target viral proteins, which ensures specificity and safety. This is a time-tested and proven concept that has led to the development of the 43 antiviral drugs in clinical use and other drugs currently under development. Unfortunately, this approach has several limitations. Drugs that target viral proteins (directly or indirectly) promptly select for resistance. For example, this has already happened with fuzeon and even with the inhibitors of CCR5-gp41 interactions. The number of potential viral targets is also limited for viruses with small genomes, such as human papillomavirus. This approach is not conducive to the prompt development of drugs against newly identified viral pathogens either, as the proteins encoded by such pathogens must first be characterized.

As an alternative to the traditional approach, the possibility of developing antiviral drugs targeting cellular proteins has recently been investigated. This approach provides several potential benefits. Inhibition of cellular proteins required for multiple viral functions could minimize the selection for resistance, for example, and a number of cellular proteins are required for replication of the viruses with the smallest genomes. Furthermore, many cellular proteins are required for replication of even distantly related viruses. Thus, drugs targeting cellular proteins could be used against a novel pathogen even before its proteins are fully characterized. However, targeting cellular proteins could also lead to unwanted negative side-effects, as such targets are commonly expressed in many uninfected cells.

SUMMARY

Described herein are compounds and methods that prevent the viral infection of cells or to treat a subject infected by a virus. The compounds and methods described herein minimize viral resistance and maximize the number of targeted viruses. Additionally, the compounds and methods minimize the toxicity to uninfected cells. The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
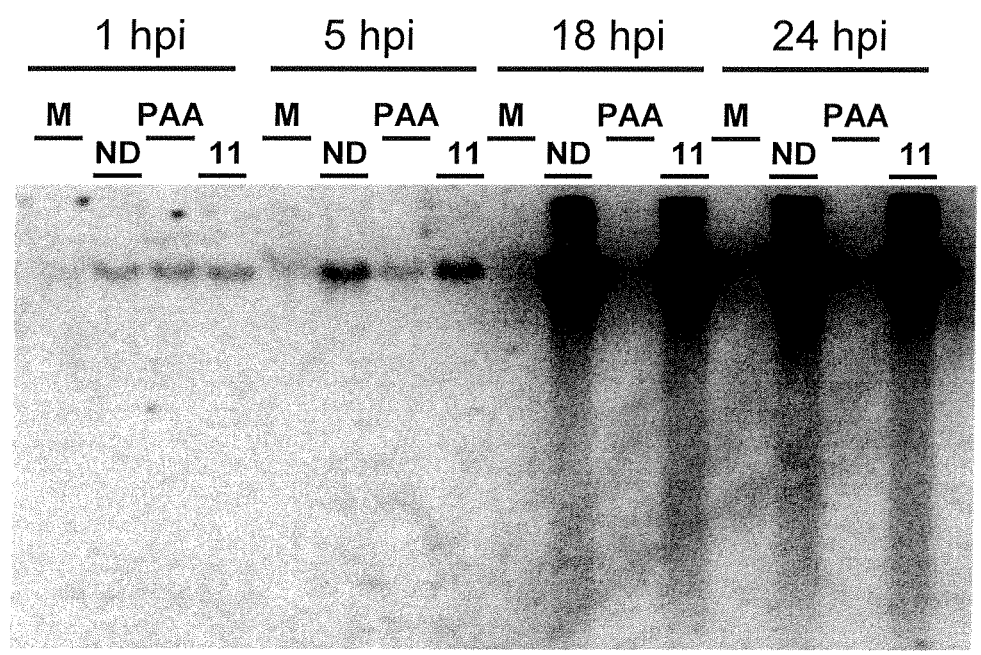
FIG. 1 shows Southern blot analyses, which indicate that amphipathic nucleoside derivative dUY11 does not inhibit HSV-1 DNA replication.

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or can not be substituted and that the description includes both unsubstituted lower alkyl and lower alkyl where there is substitution.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

By "subject" is meant an individual. The subject can be a mammal such as a primate or a human. The term "subject" can include domesticated animals including, but not limited to, cats, dogs, etc., livestock (e.g., cattle, horses, pigs, sheep, goats, etc.), and laboratory animals (e.g., mouse, rabbit, rat, guinea pig, etc.).

By "contacting" is meant an instance of exposure by close physical contact of at least one substance to another substance. For example, contacting can include contacting a substance, such as a pharmacologic agent, with a cell or a virus.

"Treatment" or "treating" means to administer a composition to a subject or a system with an undesired condition (e.g., viral infection) to reduce the symptoms of the undesired condition. "Preventing" or "prevention" means eliminating the possibility of contracting the undesired condition. "Preventing" or "prevention" also includes decreasing the possibility of contracting the undesired condition.

By "effective amount" is meant a therapeutic or preventive (prophylactic) amount needed to achieve the desired result or results.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. For example, a saccharide that contains at least one —OH group can be represented by the formula Z—OH, where Z is the remainder (i.e., residue) of the saccharide molecule.

The term "alkyl group" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is an alkyl group containing from one to six carbon atoms.

The term "aryl group" as used herein is any carbon-based aromatic group including, but not limited to, benzene, naphthalene, etc. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy. The term "aryl group" also includes two or more aromatic groups fused to one another. For example, the fused aryl group can be composed of 3, 4, 5, 6, 7, or 8 aryl rings. The fused aryl group may be unsubstituted or substituted with one or more groups described above.

The term "polyether group" as used herein is a group having the formula —[(CHR)$_n$O]$_m$—, where R is hydrogen or a lower alkyl group, n is an integer of from 1 to 20, and m is an integer of from 1 to 100. Examples of polyether groups include, polyethylene oxide, polypropylene oxide, and polybutylene oxide.

The term "polythioether group" as used herein is a group having the formula —[(CHR)$_n$S]$_m$—, where R is hydrogen or a lower alkyl group, n is an integer of from 1 to 20, and m is an integer of from 1 to 100.

The term "polyimino group" as used herein is a group having the formula —[(CHR)$_n$NR]$_m$—, where each R is, independently, hydrogen or a lower alkyl group, n is an integer of from 1 to 20, and m is an integer of from 1 to 100.

Variables such as X, L, L', R, Y, Z', $Z^2$, and $Z^3$ used throughout the application are the same variables as previously defined unless stated to the contrary.

I. Compounds and Preparation Thereof

Described herein are compounds that prevent or reduce the probability of a virus from infecting a cell. In one aspect, the compound comprises the formula I

X-L-Y    I wherein X comprises a residue of a saccharide;
L comprises a linker, wherein the linker comprises a planar hydrophilic group; and
Y comprises a planar hydrophobic group, wherein Y is directly or indirectly attached to L,
or the pharmaceutically-acceptable salt or ester thereof.

Each component of formula I will be discussed in detail. With respect to X, X comprises a residue of a saccharide. Saccharides generally possess one or more hydroxyl groups. Thus, X is a hydrophilic portion of the compound I. In one aspect, the saccharide comprises a monosaccharide. The monosaccharide can be a straight-chain monosaccharide or can be the cyclic structure (hemiacetal or hemiketal). Thus, the monosaccharide can include the furanose and pyranose forms of the monosaccharide. Examples of pentose sugars useful herein include, but not limited, to ribose, arabinose, deoxyribose, xylose, lyxose, ribulose, or xylulose. Examples of hexoses include, but not limited to, glucose, galactose, mannose, gulose, idose, talose, allose, altrose, fructose, sorbose, tagatose, psicose, fucose, or rhamnose.

In another aspect, X is a disaccharide. Disaccharides are composed of two monosaccharide units bound together by a covalent glycosidic bond. Examples of disaccharides useful herein include, but are not limited to, sucrose, lactose, trehalose, or maltose. In a further aspect, the saccharide includes an oligosaccharide or polysaccharide. Oligosaccharides and polysaccharides are composed of longer chains of monosaccharide units bound together by glycosidic bonds. The distinction between the two is based upon the number of monosaccharide units present in the chain. Oligosaccharides typically contain between two and nine monosaccharide units, and polysaccharides contain ten or more monosaccharide units. Examples of polysaccharides include, but are not limited to, glycogen, starch, cellulose, chitin, amylase, amylopectin, stachyose, inulin, or dextrin. Polysaccharides also include glycosaminoglycans (GAGs) such as, for example, heparin, chondroitin sulfate, hyaluronan, heparan sulfate, dermatan sulfate, or keratan sulfate.

Any of the hydroxyl groups present on the saccharide can be derivatized as needed using techniques known in the art. For example, a hydroxyl group can be substituted with a polyether group, polyimino group, an acetyl group, or polythioether group. Thus, the amount or degree of hydrophilicity of the saccharide can be varied as needed.

The saccharide X is covalently attached to linker L. The linker L is a planar hydrophilic group. The linker is generally flat and rigid. For example, the linker can include a residue of a purine or pyrimidine. It is also contemplated that the linker can be two or more base pairs covalently attached to one another. In one aspect, X-L can be one of the following nucleosides: adenosine, deoxyadenosine, guanosine, deoxyguanosine, 5-methyluridine, deoxythymidine, uridine, deoxyuridine, cytidine, or deoxycytidine. In one aspect, X-L in formula I is not a residue of a deoxy uridine or a derivative thereof as shown below

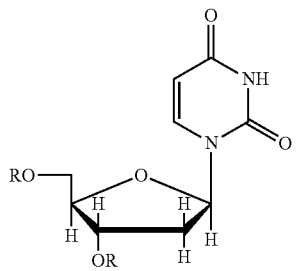

where R is hydrogen or protecting group such as, for example, an acetyl group.

In another aspect, the linker comprises a hydrophilic aryl group. For example, the aryl group can be heteroaryl group as defined herein (e.g., a pyridyl group). In other aspects, the aryl group can be substituted with one or more groups that increase the hydrophilicity of the aryl group. For example, the aryl group can be a hydroxylated aryl group or a derivative thereof. A hydroxylated aryl group is defined herein as any aryl group with at least one hydroxyl group directly attached to the aromatic ring or indirectly attached via a tether. Derivatives of the hydroxylated aryl group include any groups that modify (i.e., increase or decrease) the hydrophilicity of the aryl group. For example, the hydroxyl group can be substituted with a polyether group, polyimino group, or polythioether group as discussed above for X.

Figure 4:
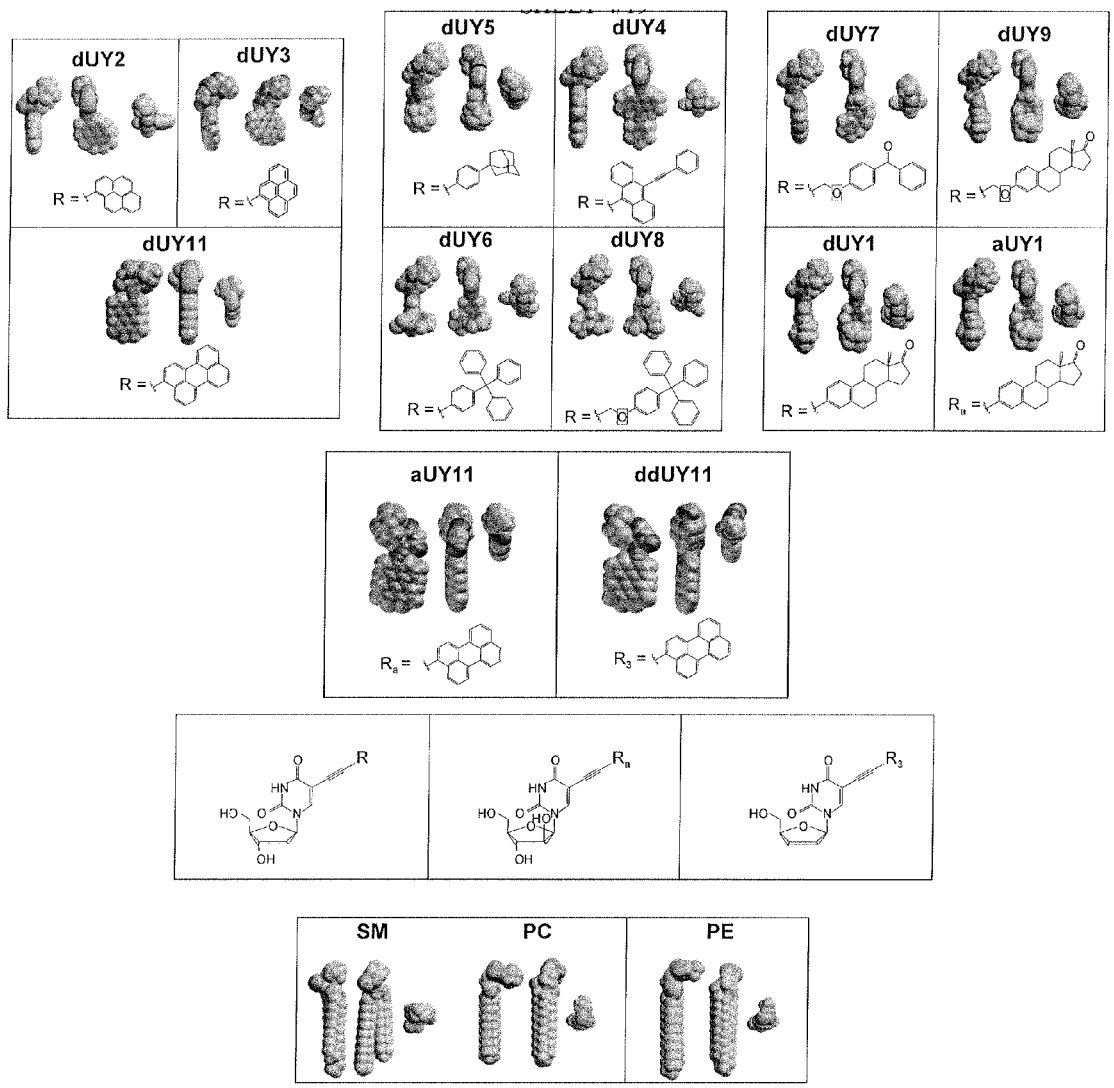
FIG. 4 shows the chemical and three dimensional structures of the amphipathic nucleoside derivatives in comparison to those of representative membrane lipids.

In formula I, Y comprises a planar hydrophobic group, wherein Y is directly or indirectly attached to L. In one aspect, Y comprises an aryl group. The aryl group in Y can assume several forms. For example, the aryl group can be a substituted or unsubstituted fused system. Examples of fused aryl groups include, but are not limited to, anthracene, phenanthrene, naphthalene, benzonaphthene, fluorine, or carbazole. In other aspects, the aryl group can be part of a larger molecule. The aryl group can be substituted with one or more different groups to modify the overall hydrophobicity of the group. Examples of aryl groups useful herein are shown in FIG. 4 with the exception of dUY7, which showed no ability to prevent viral infection as indicated in FIG. 5C.

The linker L can be directly or indirectly attached to Y. The phrase "directly attached" is defined herein is when Y is covalently attached to the linker. Conversely, the phrase "indirectly attached" is defined herein is when Y is covalently attached to the linker via a second linker (L'). The second linker L' can include, but is not limited to, an alkyl group, an alkenyl group, or an ether group (e.g., a polyether). In one aspect, L' is an alkynyl group. For example, L' can be a propargyl group or a propargyl ether group. Referring to structures A and B in FIG. 4, the alkynyl group RC≡C is attached to C5 of thymine, where R is an aryl group (i.e., group Y).

In one aspect, the compound comprises the formula II

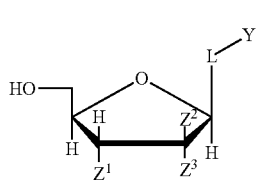

wherein $Z^1$, $Z^2$, and $Z^3$ are, independently, H or OH;
L comprises a purine or pyrimidine; and
Y comprises an aryl group,
or a derivative thereof.

In one aspect, Z is OH, L is a residue of uracil, and Y comprises an aryl group in Formula II. In another aspect, the compound has the formula IIIA or IIIB

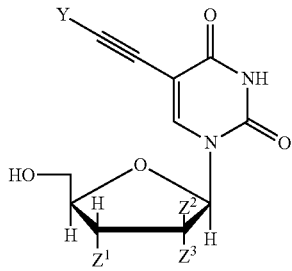

IIIA

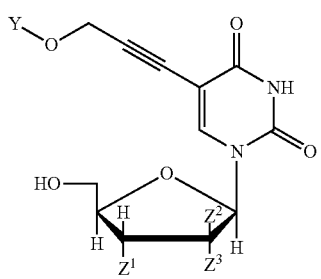

IIIB wherein $Z^1$, $Z^2$, and $Z^3$ are, independently, H or OH and Y comprises an aryl group. In a further aspect, Y comprises a fused aryl group comprising three or more aryl rings. An example of such an aryl group has the structure

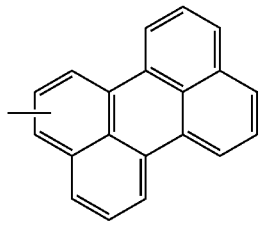

wherein the aryl group is substituted or unsubstituted.

In one aspect, the compound has the formula IIIA, where $Z^1$ is OH, $Z^2$ and $Z^3$ are hydrogen, and Y is an aryl group having the formula

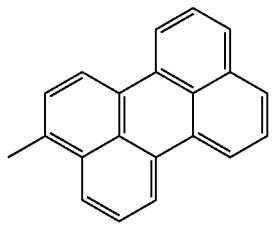 [SMILES: Cc1ccc2c3cccc4cccc(c5cccc1c52)c43]

wherein the aryl group is substituted or unsubstituted. This compound is referred to herein as dUY11. In another aspect, the compound has the formula IIIA, where $Z^1$, $Z^2$ and $Z^3$ are hydrogen, and Y is an aryl group having the formula

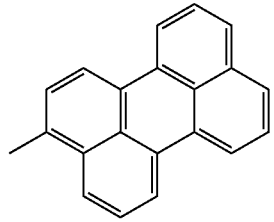 [SMILES: Cc1ccc2c3cccc4cccc(c5cccc1c52)c43]

wherein the aryl group is substituted or unsubstituted. This compound is referred to herein as ddUY11. In a further aspect, the compound has the formula IIIA, where $Z^1$ and $Z^3$ are OH, $Z^2$ is hydrogen, and Y is an aryl group having the formula

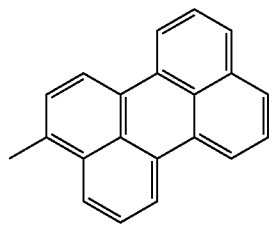 [SMILES: Cc1ccc2c3cccc4cccc(c5cccc1c52)c43]

wherein the aryl group is substituted or unsubstituted. This compound is referred to herein as aUY11.

Any of the compounds described herein can exist or be converted to the salt thereof. In one aspect, the salt is a pharmaceutically acceptable salt. The salts can be prepared by treating the free acid with an appropriate amount of a chemically or pharmaceutically acceptable base. Representative chemically or pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. In one aspect, the reaction is conducted in water, alone or in combination with an inert, water-miscible organic solvent, at a temperature of from about 0° C. to about 100° C. such as at room temperature. The molar ratio of the compound to base used is chosen to provide the ratio desired for any particular salts. For preparing, for example, the ammonium salts of the free acid starting material, the starting material can be treated with approximately one equivalent of base to yield a salt.

In another aspect, any of the compounds described herein can exist or be converted to the salt with a Lewis base thereof. The compounds can be treated with an appropriate amount of Lewis base. Representative Lewis bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, tetrahydrofuran, ether, thiol reagent, alcohols, thiol ethers, carboxylates, phenolates, alkoxides, water, and the like. In one aspect, the reaction is conducted in water, alone or in combination with an inert, water-miscible organic solvent, at a temperature of from about 0° C. to about 100° C. such as at room temperature. The molar ratio of the compound to base used is chosen to provide the ratio desired for any particular complexes. For example, the ammonium salts of the free acid starting material, the starting material can be treated with approximately one equivalent of chemically or pharmaceutically acceptable Lewis base to yield a complex.

If the compounds possess carboxylic acid groups, these groups can be converted to pharmaceutically acceptable esters or amides using techniques known in the art. Alternatively, if an ester is present, the ester can be converted to a pharmaceutically acceptable ester using transesterification techniques.

The compounds described herein can be synthesized using techniques known in the art. For example, when X-L is a nucleoside, it can be coupled with Y or Y-L' to produce the compound having formula I.

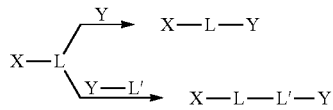

In one aspect, when X-L is a nucleoside as depicted in formula IV, a coupling reaction can be used to produce the compound V.

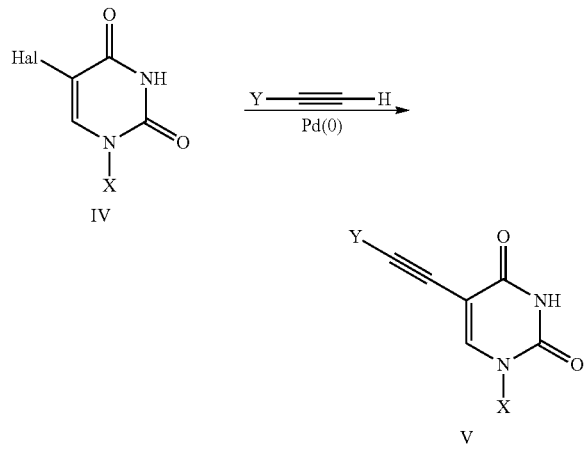

In this aspect, X is the saccharide and Hal is a halogen such as iodide. A palladium catalyst is used to couple the alkyne Y—C≡CH with compound IV to produce compounds having the formula V.

II. Pharmaceutical Compositions

In one aspect, any of the compounds described above can be formulated into a pharmaceutical composition. The pharmaceutical compositions can be prepared using techniques known in the art. In one aspect, the composition is prepared by admixing a compound described herein with a pharmaceutically-acceptable carrier.

It will be appreciated that the actual preferred amounts of active compound having the formula I in a specified case will vary according to the specific compound being utilized, the particular compositions formulated, the mode of application, and the particular sites and subject being treated. Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physicians Desk Reference, Barnhart Publishing—1999).

Pharmaceutical compositions described herein can be formulated in any excipient the biological system or entity can tolerate. Examples of such excipients include, but are not limited to, water, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity-enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosol, cresols, formalin and benzyl alcohol.

Pharmaceutical carriers are known to those skilled in the art. These most typically would be standard carriers for administration to humans, including solutions such as sterile water, saline, and buffered solutions at physiological pH.

Molecules intended for pharmaceutical delivery can be formulated in a pharmaceutical composition. Pharmaceutical compositions can include carriers, thickeners, diluents, buffers, preservatives, surface-active agents and the like in addition to the molecule of choice.

The pharmaceutical composition can be administered in a number of ways depending on whether local or systemic treatment is desired, and on the area to be treated. Administration can be topically (including ophthalmically, vaginally, rectally, intranasally, vaporization). Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Preparations for administration include sterile aqueous or non-aqueous solutions, suspensions, and emulsions. Examples of aqueous carriers include water, alcoholic/aqueous solutions, emulsions or suspensions, including saline and buffered media. Parenteral vehicles, if needed for collateral use of the disclosed compositions and methods, include sodium chloride solution, Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

The pharmaceutical compositions can also include other drugs and biologically-active agents. The biologically-active agent is capable of providing a local or systemic biological, physiological or therapeutic effect in the biological system. For example, the agent can act to control infection or inflammation, enhance cell growth and tissue regeneration, control tumor growth, act as an analgesic, and enhance bone growth, among other functions. Thus, combination therapies are contemplated where the compositions described herein can reduce or prevent viral infection in combination with other therapeutic benefits.

III. Methods of Use

The compounds and pharmaceutical compositions described herein can be used in a variety of applications related to the prevention or treatment of viral infection. A method for preventing a virus from infecting cells includes contacting the virus or a previously infected cell with the compound comprising the formula X-L-Y (I) as defined above.

Viruses are classified as enveloped or non-enveloped, according to whether their capsids are surrounded by a host-cell derived lipid bilayer membrane (the envelope) or not. Although the viral envelope derives from cellular membranes, the two lipid bilayers display major intrinsic differences. Functionally, the cellular membranes are selective physical barriers required to separate the intra- and extracellular environments, while allowing the selective passage of certain molecules. In contrast, the major functions of the viral envelope are to fuse with the cellular membranes and to hide most viral proteins from the immune system of the host. Although the viral envelope may confer some physical protection under limited circumstances, enveloped viruses are most often less resistant to physical or chemical injuries than non-enveloped ones. Structurally, both the lipid and protein composition of the virion envelope and cellular membranes are different, as are their curvatures and fluidities.

The compounds described herein can be referred to as amphipathic, where a moiety of the molecule is hydrophilic (X-L) and another moiety is hydrophobic (Y). Not wishing to be bound by theory, it is believed that the compounds described herein prevent fusion of the enveloped virus with the cell membrane, which ultimately prevents the entry of the virus into the cell. The hydrophobic moiety of the compounds described herein (i.e., Y) can insert itself in the hydrophobic core of the lipid envelope. The hydrophilic moiety (i.e., X) interacts with the polar heads on the surface of the envelope. Thus, the compounds are phospholipid-mimetics. However, the antiviral compounds described herein possess shapes that are more markedly inverted conical than the shapes of the naturally occurring lipids in the outer leaflets of virion envelopes. Inverted cone lipids in the outer leaflet of the envelope inhibit the curvature transitions required for fusion between membranes. The amphipathic compounds can therefore inhibit fusion between the viral envelope and the plasma membrane of the cell. The hydrophobic moiety of formula I (Y), the hydrophilic moiety and the general molecular shape of the compounds can be easily optimized to interact preferentially with the viral envelope over the cellular membrane. The compounds described herein can also be designed to prevent any potential incorporation into replicating DNA. Examples of such modifications can be seen in compounds ddUY11 and aUY11 (see Examples). In the case of ddUY11, a hydroxyl in the sugar moiety has been removed from dUY11 to produce ddUY11. With aUY11, the deoxy-ribose sugar of dUY11 was replaced with an arabino sugar.

The viruses that can be targeted are non-specific. Viruses that can be targeted include enveloped viruses such as, for example, poxviruses, herpes simplex virus types 1 or 2 (HSV-1, HSV-2), influenza virus, HIV, human T cell leukemia virus (HTLV), Epstein-Barr virus (EBV), human cytomegalovirus (HCMV), Kaposi's sarcoma-associated herpesvirus (KSHV), varicella-zoster virus (VZV), hepatitis B virus, hepatitis C virus, Ebola virus, Marburg virus, parainfluenza virus, human respiratory syncitial virus, Hendra virus, Nipah virus, mumps virus, measles virus, Hantavirus, Bunyavirus, Rift Valley fever virus, Arenaviruses, including sin nombre virus, rabies virus, Eastern, Western and Venezuelan encephalitis viruses, West Nile virus, yellow fever virus, Dengue virus, Japanese and St. Louis encephalitis virus, coronaviruses (e.g., SARS virus), or rubellavirus.

The compounds described herein can be used to prevent or reduce viral infection. In one aspect, described herein is a method for preventing or reducing the probability of a virus from infecting a subject, comprising administering to the subject in need of such treatment an effective amount of a compound comprising the formula I. The compound can be administered using any of the techniques described above. In one aspect, the compound is applied to an infection site. The term "infection site" is one or more body parts of the subject that if comes into contact with a virus the subject is infected. Examples of such infection sites include mucosal linings (e.g., vaginal, rectum, nasal passageways). Thus, in one aspect, the compounds described herein can be used as prophylactics in the prevention of sexually-transmitted diseases. In this aspect, the compound is formulated as a topical formulation (e.g., gel, lotion, or cream) that can be directly or indirectly applied to the vagina or rectum. In another aspect, the compounds described herein can be used as prophylactics in the prevention of respiratory diseases. In this aspect, the compound can be formulated as a spray that can be applied to the respiratory tract.

The compounds described herein can be used as therapeutics to treat a subject infected with a virus. In one aspect, the method comprises administering an effective amount of a compound comprising the formula X-L-Y (I) to a subject in need of such treatment. The compounds described herein can reduce the infectious properties of the virus, which ultimately can reduce the spread of the virus as well as the symptoms of the disease produced by the virus. When used as a therapeutic, the compounds can be administered in a number of ways including orally, parenterally, or topically.

The compounds described herein can be used to prevent or reduce the probability of a virus in the environment from infecting a subject. The method involves decontaminating the environment with one or more compounds comprising the formula I. The environment involves any setting or substrate (e.g., a medical device) that has been in contact with the virus. For example, the compounds described herein can be sprayed on a substrate exposed to one or more viruses where the compound comes into contact with the virus. As another example, the compound can be in a solution, where the substrate is submerged into the solution, or the solution is placed into the substrate (e.g., tubing or other restricted spaces), to inactivate any potential virions present on the substrate.

In another aspect, the compounds described herein can be used to inactivate virions to produce a vaccine. The method involves contacting the virus with one or more compounds comprising the formula I as defined above. The inactivated virions can then be administered as a vaccine using techniques known in the art.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

I. Preparation of Compounds Having the Formula I a. Procedure 1

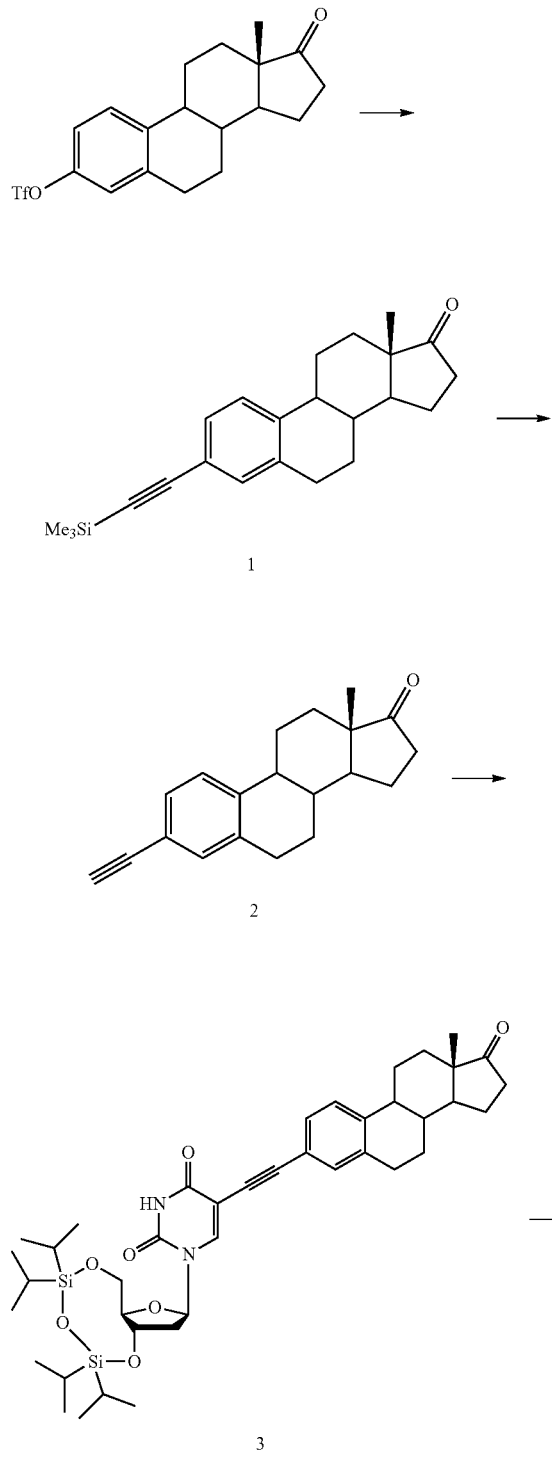

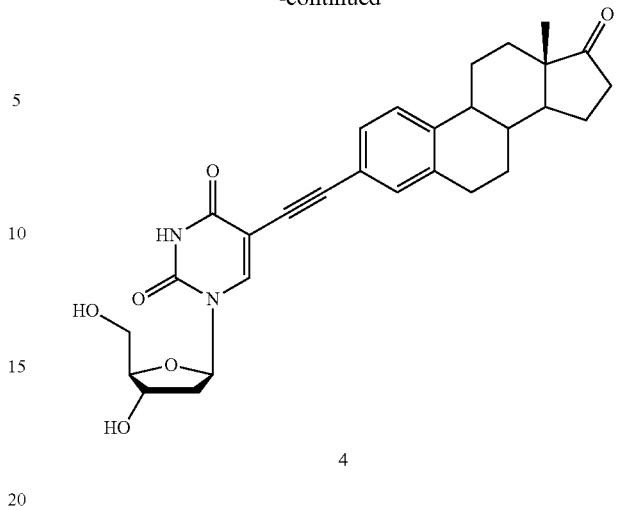

3-(Trimethylsilylethynyl)estrone (1)

A solution of 3-O-trifluoromethylsulfonylestrone (972 mg, 2.41 mmol) in DMF (10 mL) was degassed three times by alternating between vacuum and argon. Trimethylsilylacetylene (0.68 mL, 4.82 mmol), tetrakis(triphenylphosphine)palladium (279 mg, 0.24 mmol), copper (I) iodide (93 mg, 0.48 mmol) and triethylamine (0.67 mL, 4.82 mmol) were added and the mixture was stirred for 48 h. After that the mixture was poured into water (100 mL) and EtOAc (200 mL), the organic layer was washed with water (4×100 mL), 0.1 M aqueous $Na_2EDTA$ (2×100 mL) and water (2×100 mL), brine (100 mL), dried over $Na_2SO_4$ and evaporated. The residue was subjected to column chromatography (silica gel, 1% to 4% EtOAc in PhMe) to give the title product as colorless solid. Yield 790 mg (94%). $^1H$ NMR ($CDCl_3$): 0.26 (s, 9H), 0.94 (s, 3H), 1.40-1.71 (m, 6H), 1.96-2.58 (m, 7H), 2.86-2.95 (m, 2H), 7.21-7.30 (m, 3H).

3-Ethynylestrone (2)

Tetrabutylammonium fluoride trihydrate (1.23 g, 3.9 mmol) was added to a stirred solution of 3-(trimethylsilylethynyl)estrone (697 mg, 1.95 mmol) under argon. The mixture was stirred at rt for 4 h and evaporated. The residue was subjected to column chromatography (silica gel, 5% to 7% EtOAc in PhMe) to give the title product as off-white solid. Yield 530 mg (98%). $^1H$ NMR ($CDCl_3$): 0.94 (s, 3H), 1.41-1.72 (m, 6H), 1.95-2.59 (m, 7H), 2.88-2.96 (m, 2H), 3.04 (s, 1H), 7.24-7.33 (m, 3H).

3',5'-O-Tetraisopropyldisiloxane-1,3-diyl-5-(estrone-3-ylethynyl)-2'-deoxyuridine (3)

A solution of 3-ethynylestrone (61 mg, 0.215 mmol) and 3',5'-O-tetraisopropyldisiloxane-1,3-diyl-5-iodo-2'-deoxyuridine (117 mg, 0.196 mmol) in DMF (10 mL) was degassed three times by alternating between vacuum and argon. Tetrakis(triphenylphosphine)palladium (23 mg, 0.02 mmol), copper (I) iodide (4 mg, 0.04 mmol) and triethylamine (0.10 mL, 0.39 mmol) were added and the mixture was stirred for 48 h. After that the mixture was poured into water (100 mL) and EtOAc (200 mL), the organic layer was washed with water (4×100 mL), 0.1 M aqueous $Na_2EDTA$ (2×100 mL) and water (2×100 mL), brine (100 mL), dried over $Na_2SO_4$ and evaporated. The residue was subjected to column chromatography (silica gel, 10% EtOAc in PhMe) to give the title product as yellowish solid. Yield 79 mg (54%). $^1H$ NMR ($CDCl_3$): 0.85 (s, 3H), 0.92-1.18 (m, 28H), 1.33-1.62 (m, 6H), 1.73-1.81 (m, 1H), 1.93-2.52 (m, 8H), 2.84-2.97 (m, 2H), 3.55-3.84 (m, 1H), 4.23-4.29 (s, 2H), 6.14 (t, 1H, J=6.6 Hz), 7.20 (s, 1H), 7.32 (d, 1H, J=8.25), 7.42 (d, 1H, J=8.25), 8.33 (s, 1H).

5-(Estrone-3-ylethynyl)-2'-deoxyuridine (4)

3',5'-O-Tetraisopropyldisiloxane-1,3-diyl-5-(estrone-3-ylethynyl)-2'-deoxyuridine (70 mg, 0.093 mmol) was dissolved in THF (1 mL) and treated with triethylamine trihydrofluoride (46 μL, 0.28 mmol). The mixture was kept at rt for 24 h, and the precipitate formed was separated by centrifugation. The solid was re-crystallized from THF-MeOH to give the title compound as colorless solid. Yield 44 mg (94%). $^1$H NMR (CDCl$_3$): 0.85 (s, 3H), 1.35-1.64 (m, 6H), 1.75-1.84 (m, 1H), 1.93-2.49 (m, 8H), 2.81-2.97 (m, 2H), 3.56-3.85 (m, 3H), 4.23-4.29 (s, 2H), 6.14 (t, 1H, J=6.6 Hz), 7.20 (s, 1H), 7.32 (d, 1H, J=8.25), 7.42 (d, 1H, J=8.25), 8.34 (s, 1H).

b. Procedure 2

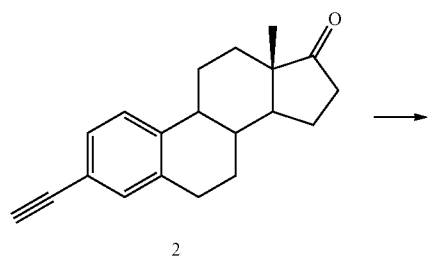

2

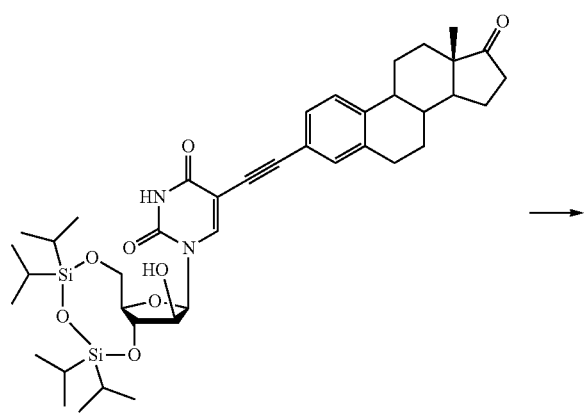

5

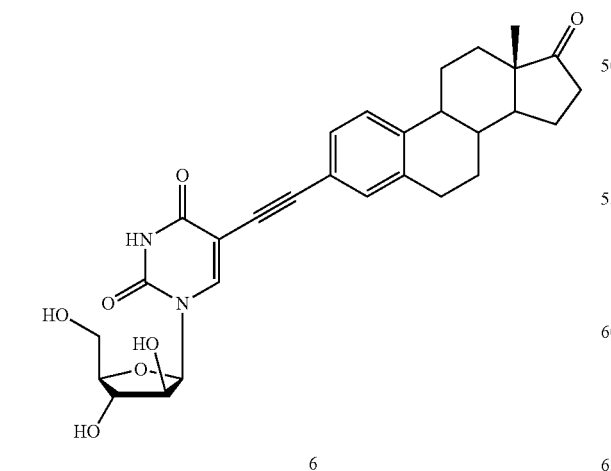

6

3',5'-O-Tetraisopropyldisiloxane-1,3-diyl-5-(estrone-3-ylethynyl)-arabino-uridine (5)

A solution of 3-ethynylestrone (100 mg, 0.36 mmol) and 3',5'-O-tetraisopropyldisiloxane-1,3-diyl-5-iodo-arabino-uridine (197 mg, 0.32 mmol) in DMF (7 mL) was degassed three times by alternating between vacuum and argon. Tetrakis(triphenylphosphine)palladium (38 mg, 0.032 mmol), copper (I) iodide (7 mg, 0.064 mmol) and triethylamine (0.17 mL, 0.64 mmol) were added and the mixture was stirred for 48 h. After that the mixture was poured into water (100 mL) and EtOAc (200 mL), the organic layer was washed with water (4×100 mL), 0.1 M aqueous Na$_2$EDTA (2×100 mL) and water (2×100 mL), brine (100 mL), dried over Na$_2$SO$_4$ and evaporated. The residue was subjected to column chromatography (silica gel, 20% Me$_2$CO in PhMe) to give the title product as yellowish solid. Yield 70 mg (29%). $^1$H NMR (CDCl$_3$): 0.85 (s, 3H), 0.92-1.17 (m, 28H), 1.35-1.64 (m, 6H), 1.74-1.82 (m, 1H), 1.92-2.49 (m, 6H), 2.81-2.89 (m, 2H), 3.66-3.89 (m, 1H), 3.88-4.16 (m, 5H), 6.08 (d, 1H, J=6.41 Hz), 7.17 (s, 1H), 7.20 (d, 1H, J=8.25), 7.33 (d, 1H, J=8.25), 7.66 (s, 1H), 11.7 (br. s).

5-(Estrone-3-ylethynyl)-arabino-deoxyuridine (6)

3',5'-O-Tetraisopropyldisiloxane-1,3-diyl-5-(estrone-3-ylethynyl)-arabino-uridine (70 mg, 0.091 mmol) was dissolved in THF (1 mL) and treated with triethylamine trihydrofluoride (44 μL, 0.27 mmol). The mixture was kept at rt for 24 h, and the precipitate formed was separated by centrifugation. Colorless solid. Yield 41 mg (87%). $^1$H NMR (CDCl$_3$): 0.85 (s, 3H), 1.31-1.62 (m, 6H), 1.74-1.83 (m, 1H), 1.90-2.51 (m, 6H), 2.80-2.90 (m, 2H), 3.66-3.89 (m, 2H), 3.91-4.13 (m, 6H), 6.08 (d, 1H, J=6.41 Hz), 7.17 (s, 1H), 7.20 (d, 1H, J=8.25), 7.33 (d, 1H, J=8.25), 7.62 (s, 1H), 11.5 (br. s).

c. Procedure 3

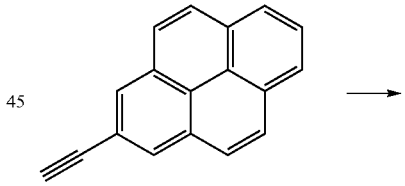

7

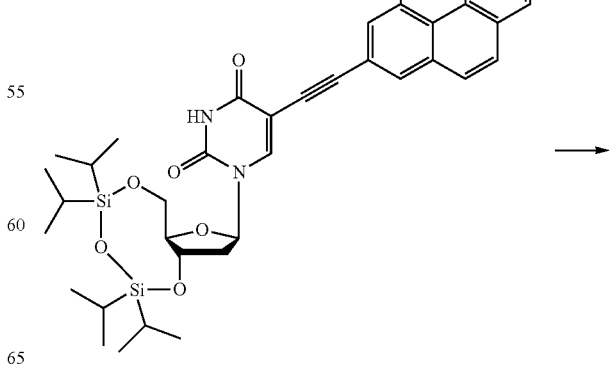

8

-continued

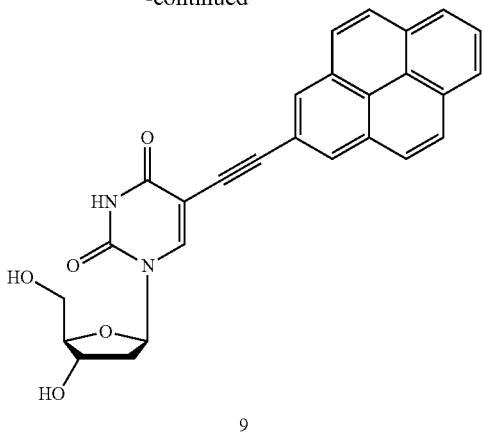

3',5'-O-Tetraisopropyldisiloxane-1,3-diyl-5-(pyrene-2-ylethynyl)-2'-deoxyuridine (8)

A solution of 2-ethynylpyrene (345 mg, 1.53 mmol) and 3',5'-O-tetraisopropyldisiloxane-1,3-diyl-5-iodo-2'-deoxyuridine (758 mg, 1.27 mmol) in DMF (10 mL) was degassed three times by alternating between vacuum and argon. Tetrakis(triphenylphosphine)palladium (147 mg, 0.127 mmol), copper (I) iodide (48 mg, 0.25 mmol) and triethylamine (0.35 mL, 2.54 mmol) were added and the mixture was stirred for 24 h. After that the mixture was poured into water (100 mL) and EtOAc (200 mL), the organic layer was washed with water (4×100 mL), 0.1 M aqueous Na$_2$EDTA (2×100 mL) and water (2×100 mL), brine (100 mL), dried over Na$_2$SO$_4$ and evaporated. The residue was subjected to column chromatography (silica gel, 0% to 5% EtOAc in CHCl$_3$) to give the title product as yellowish solid. Yield 402 mg (49%). $^1$H NMR (CDCl$_3$): 0.90-1.17 (m, 28H), 2.19-2.34 (m, 2H), 3.64-3.78 (m, 2H), 3.84-3.92 (m, 1H), 4.30-4.37 (m, 1H), 6.22 (t, 1H, J=6.42 Hz), 8.09-8.49 (m, 9H), 8.62 (s, 1H), 11.8 (br. s).

5-(Pyrene-2-ylethynyl)-2'-deoxyuridine (9)

3',5'-O-Tetraisopropyldisiloxane-1,3-diyl-5-(pyrene-2-ylethynyl)-2'-deoxyuridine (200 mg, 0.29 mmol) was dissolved in THF (1 mL) and treated with triethylamine trihydrofluoride (0.14 mL, 0.86 mmol). The mixture was kept at rt for 24 h, and the precipitate was filtered off. The solid was re-crystallized from EtOH to produce a colorless solid. Yield 74 mg (56%). $^1$H NMR (CDCl$_3$): 2.19-2.34 (m, 2H), 3.64-3.76 (m, 2H), 3.84-3.91 (m, 1H), 4.29-4.34 (m, 1H), 5.23-5.32 (m, 2H), 6.22 (t, 1H, J=6.42 Hz), 8.09-8.48 (m, 9H), 8.62 (s, 1H), 11.9 (br. s).

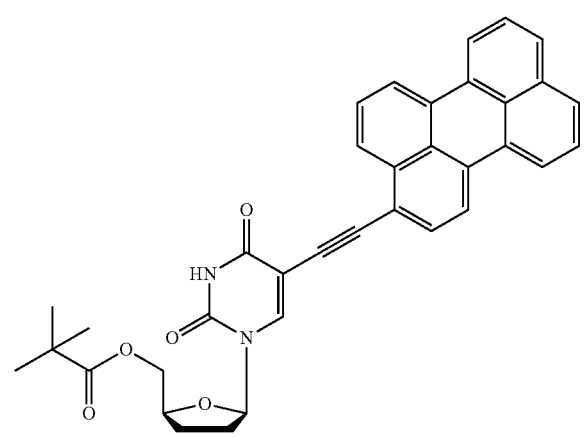

5-(Perylen-3-ylethynyl)-5'-O-pivaloyl-2',3'-dideoxyuridine

A solution of 5-iodo-5'-O-pivaloyl-2',3'-dideoxyuridine (442 mg, 1 mmol) and 3-perylenylacetylene (345 mg, 1.25 mmol) in 10 mL of DMF was degassed three times by alternation between vacuum and argon. Then Pd(PPh$_3$)$_4$ (115 mg, 0.1 mmol), CuI (38 mg, 0.2 mmol) and Et$_3$N (0.278 mL, 2 mmol) were added and the flask was degassed once again, filled with argon, and the mixture was stirred for 43 hours at ambient temperature. The mixture was diluted with 300 mL of EtOAc, washed 3×200 mL of water, dried with Na$_2$SO$_4$, and evaporated. Chromatography on a silica gel column using a 0 to 2% of EtOH/CHCl$_3$ gradient gave rise to a chromatographically homogeneous (R$_f$ 0.28, 5% EtOH/CHCl$_3$) product as orange foam (545 mg, 96%). $^1$H-NMR (DMSO-d$_6$): 11.85 (s, 1H, NH), 8.44 (d, 1H, J 7.8), 8.39-8.35 (m, 3H), 8.32 (d, 1H, J 8.2) (perylenyl), 8.06 (s, 1H, H-6), 7.83-7.81 (m, 2H), 7.69-7.60 (m, 2H), 7.58-7.53 (m, 2H) (perylenyl), 6.00 (dd, 1H, J$_{1',2'\alpha}$ 6.9 J$_{1',2'\beta}$ 4.6, H-1'), 4.37-4.34 (m, 1H, H-4'), 4.32-4.26 (m, 2H, H-5'), 2.42-2.36 (m, 1H, H-2'), 2.17-2.12 (m, 1H, H-2'), 2.06-2.00 (m, 1H, H-3'), 1.90-1.83 (m, 1H, H-3'), 1.17 (s, 9H, $^t$Bu).

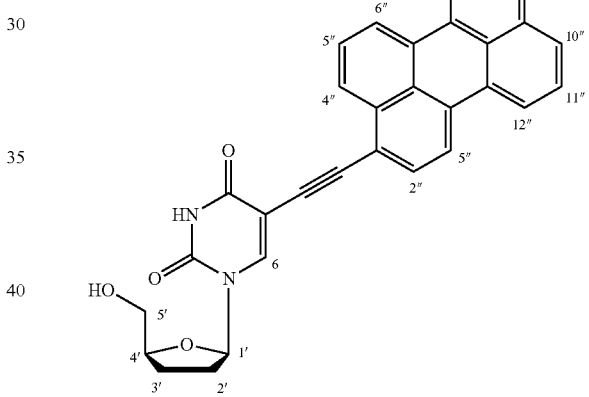

5-(Perylen-3-ylethynyl)-2',3'-dideoxyuridine (ddUY11)

To a suspension of 5-(perylen-3-ylethynyl)-5'-O-pivaloyl-2',3'-dideoxyuridine (350 mg, 0.613 mmol) in 80 mL of MeOH solid KOH (310 mg, 5.517 mmol) was added, and the mixture was stirred overnight. The mixture was then neutralized with acetic acid, evaporated under reduced pressure, co-evaporated with MeOH twice to give a crude product, which was chromatographically purified on a silica gel column using a 0 to 3% EtOH/CHCl$_3$ gradient to give a chromatographically homogeneous (R$_f$ 0.46, 37.5% acetone/CHCl$_3$) product as orange solid (130 mg, 43%). $^1$H-NMR (DMSO-d$_6$): 11.74 (s, 1H, NH), 8.76 (s, 1H, H-6), 8.45 (d, 1H, J 7.7), 8.41-8.38 (m, 2H), 8.36 (d, 1H, J 7.7), 8.30 (d, 1H, J 7.7), 7.71-7.54 (m, 6H) (perylenyl), 5.99-5.98 (m, 1H, H-1'), 5.35 (br. s, 1H, OH), 4.15-4.10 (m, 1H, H-4'), 3.70 (app. d, 1H, H-5'), 3.63 (app. d, 1H, H-5'), 2.38-2.31 (m, 1H, H-2'), 2.17-2.13 (m, 1H, H-2'), 2.01-1.94 (m, 1H, H-3'), 1.91-1.86 (m, 1H, H-3').

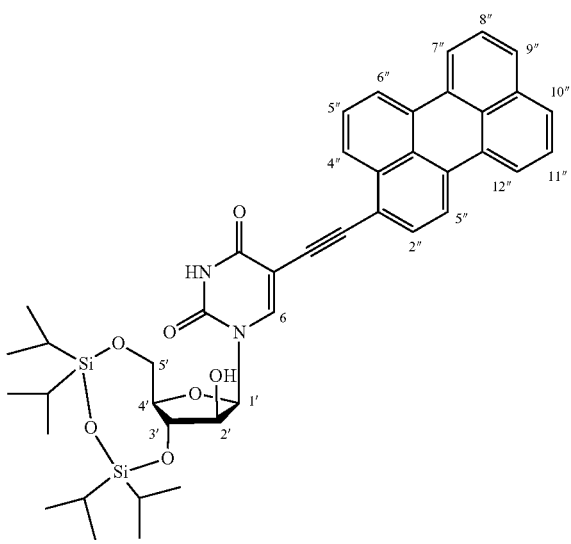

5-(Perylen-3-ylethynyl)-3',5'-O-(tetraisopropyldisiloxane-1,3-diyl)-arabino-uridine A solution of 5-iodo-3',5'-O-(tetraisopropyldisiloxane-1, 3-diyl)-arabino-uridine (612 mg, 1 mmol) and 3-perylenylacetylene (373 mg, 1.35 mmol) in 10 mL of DMF was degassed three times by alternation between vacuum and argon. Then Pd(PPh$_3$)$_4$ (115 mg, 0.1 mmol), CuI (38 mg, 0.2 mmol), and Et$_3$N (0.278 mL, 2 mmol) were added, and the flask was degassed once again, filled with argon, and th mixture was stirred for 43 hours at ambient temperature. The mixture was diluted with 300 mL of CHCl$_3$, washed 3×200 mL of water, organic layer was dried with Na$_2$SO$_4$, evaporated under reduced pressure and reevaporated with CHCl$_3$ twice. Chromatographic purification on a silica gel column in a 0 to 3% EtOH/CHCl$_3$ gradient gave chromatographically homogeneous (R$_f$ 0.6, 10% EtOH/CHCl$_3$) product as orange foam (245 mg, 32%). $^1$H-NMR (DMSO-d$_6$): 11.89 (s, 1H, NH), 8.46 (d, 1H, J 7.3), 8.43-8.34 (m, 3H), 8.26 (d, 1H, J 8.2), 7.84 (t, 2H, J 7.3) (perylenyl), 7.81 (s, 1H, H-6), 7.69-7.64 (m, 2H), 7.57 (t, 2H, J 7.8) (perylenyl), 6.12 (d, 1H, J 6.4, H-1'), 6.12 (d, 1H, J 6.0, H-b2'), 4.39 (app. q, 1H, H-4'), 4.14 (app. t, 1H, H-3'), 4.08 (app. d, 1H, H-5'), 3.93 (app. d, 1H, H-5'), 3.75 (br. d, 1H, OH), 1.07-0.95 (m, 28H, iPr).

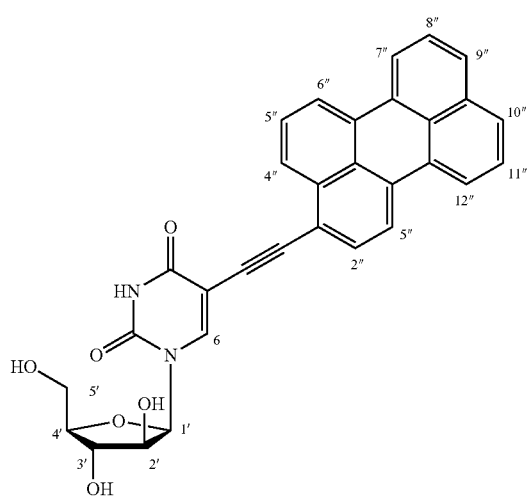

5-(Perylen-3-ylethynyl)-arabino-uridine (aUY11)

To solution of 5-(perylen-3-ylethynyl)-3',5'-O-(tetraisopropyldisiloxane-1,3-diyl)-arabino-uridine (220 mg, 0.289 mmol) in 0.8 mL of THF neat Et$_3$N.HF (0.118 mL, 0.723 mmol) was added, and the mixture was stirred for 12 hours at ambient temperature. Then, a small amount of methanol was added to precipitate the product, which was filtered and dried. Orange solid (100 mg, 67%), R$_f$ 0.30 (10% EtOH/CHCl$_3$). $^1$H-NMR (DMSO-d$_6$): 12.00-11.00 (br. s, 1H, NH), 8.46 (d, 1H, J 7.7), 8.43-8.38 (m, 2H), 8.36 (d, 1H, J 7.7), 8.30 (d, 1H, J 8.33) (perylenyl), 8.26 (s, 1H, H-6), 7.84 (t, 2H, J 7.0), 7.73 (d, 1H, J 7.7), 7.69 (t, 1H, J 7.7), 7.57 (t, 2H, J 7.7) (perylenyl), 6.07 (d, 1H, J 3.9, H-1'), 5.77-5.68 (br. s, 1H), 5.60-5.48 (br. s, 1H), 5.32-5.20 (br. s, 1H) (OH), 4.12-4.09 (app. s, 1H), 4.03-3.98 (ap. s, 1H) (H-2', H-4'), 3.82 (app. d, 1H, H-5'), 3.74-3.67 (m, 2H, H-3',5').

II. Amphipathic Nucleoside Derivatives do Not Inhibit HSV-1 DNA Replication or the Release of Virions by Infected Cells Nucleoside or nucleotide derivatives typically inhibit HSV-1 DNA replication by targeting the viral DNA polymerase. To identify whether the amphipathic nucleoside derivatives inhibited either viral DNA replication or viral gene expression, the ability of the amphipathic nucleoside derivatives to inhibit the accumulation of HSV-1 DNA was tested. Vero cells were mock infected (M) or infected with 5 plaque-forming-units (PFU)/cell of wild-type HSV-1 for 1 h, washed, and overlaid with medium containing no drug (ND), 400 μM of phosphonoacetic acid (PAA) or 2 μM of a representative amphipathic nucleoside derivative, dUY11 (11) (FIG. 4). Cells were harvested at 1, 5, 18 or 24 hours post infection (hpi), DNA was isolated, resolved by agarose gel electrophoresis, transferred onto a nitrocellulose membrane, and hybridized with the 6 kb BamK HSV-1 fragment. Southern blot analyses (FIG. 1) show the levels of intracellular viral DNA at 1, 5, 18 and 24 hpi. dUY11 does not inhibit viral DNA replication at any time tested.

Figure 2:
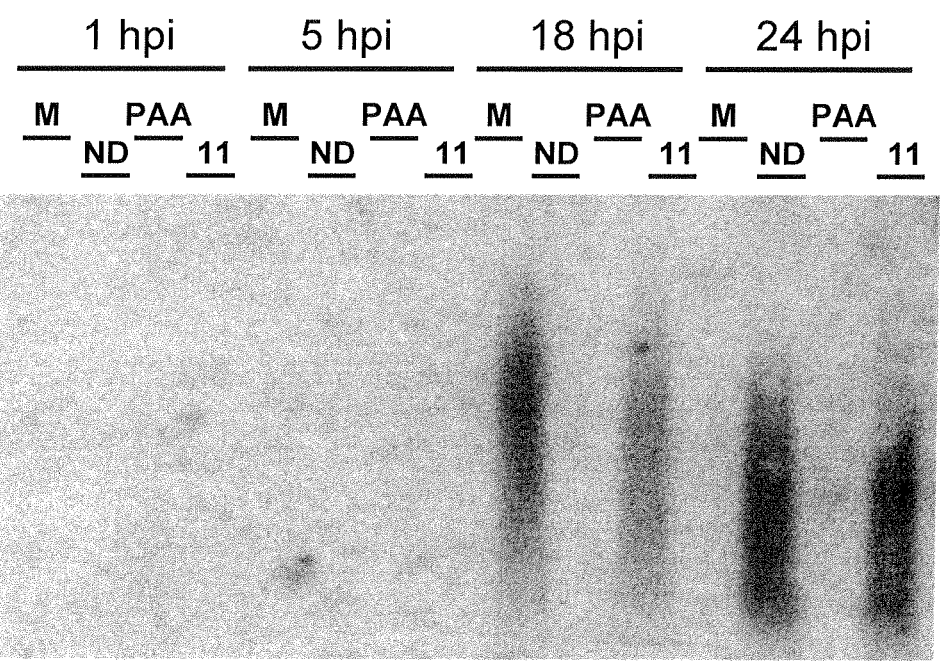
FIG. 2 shows Southern blot analyses, which indicate that amphipathic nucleoside derivative dUY11 does not inhibit the release of progeny HSV-1 DNA.

The ability of amphipathic nucleoside derivatives to inhibit the release of HSV-1 virions by infected cells was tested next. Vero cells were mock infected (M) or infected with 5 PFU/cell of wild-type HSV-1 for 1 h, washed, and overlaid with medium containing no drug (ND), 400 μM of phosphonoacetic acid (PAA) or 2 μM of a representative amphipathic nucleoside derivative, dUY11 (11). Supernatants from infected cells were harvested at 1, 5, 18 or 24 hpi, DNA was isolated, resolved by agarose gel electrophoresis, transferred onto a nitrocellulose membrane, and hybridized with the 6 kb BamK HSV-1 fragment. Southern blot analyses (FIG. 2) show the levels of extracellular viral DNA at 1, 5, 18 and 24 hpi. dUY11 does not inhibit the release of HSV-1 DNA. Based on these findings, viral DNA is replicated and progeny virions are released from cells infected in the presence of these amphipathic nucleoside derivatives.

Figure 3:
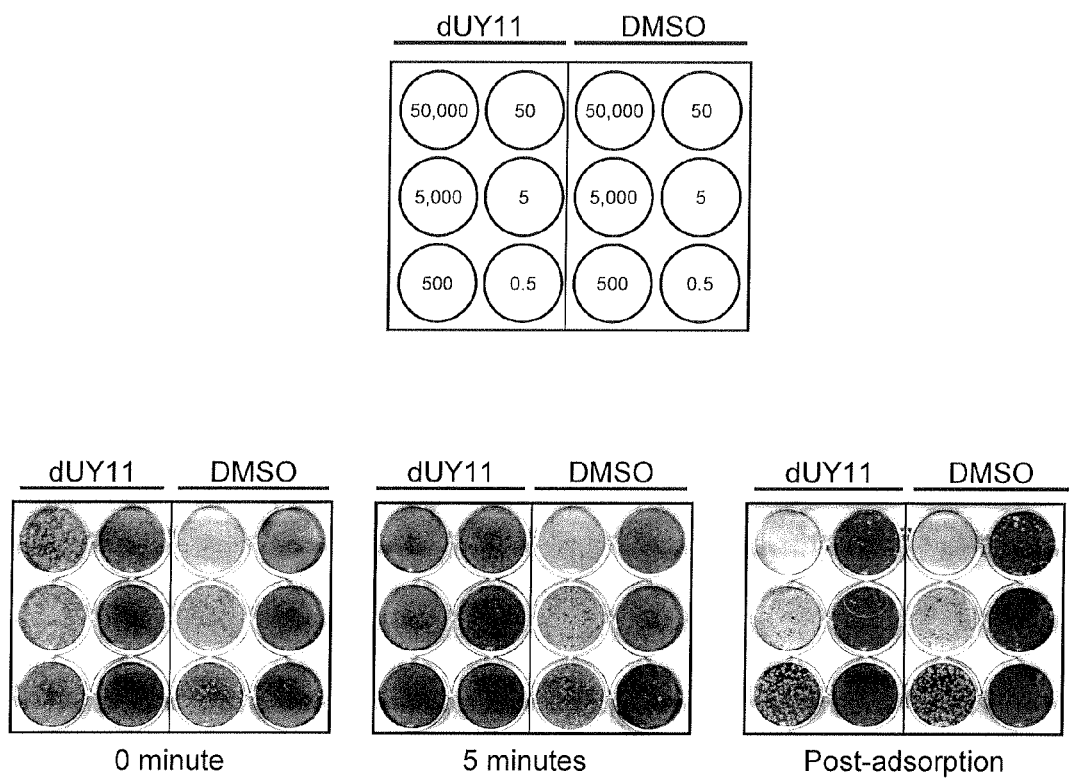
FIG. 3 shows a plaque assay revealing the inhibitory properties of dUY11 on viral infectivity.

III. The Amphipathic Nucleoside Derivatives Inhibit Infectivity of Mature Virions Infectivity and plaque assays (FIG. 3) revealed the inhibitory properties of dUY11 on viral infection. HSV-1 inocula were incubated at 37° C. for 0 or 5 minutes with 2 μM of dUY11 (left half of each panel) or with DMSO vehicle (right half of each panel). Vero cells were infected with 0.5; 5; 50; 500; 5,000; or 50,000 PFU of treated HSV-1, as indicated in the cartoon (top panel), washed and overlaid with Dulbecco's Modified Eagle Media (DMEM) supplemented with 5% fetal bovine serum (FBS) and 2% methylcellulose (MC). The samples presented in the rightmost panel were infected with untreated virions in the absence of dUY11 and overlaid with 1% MC in DMEM-5% FBS supplemented with 2 µM dUY11 (Post-adsorption). dUY11 inhibits viral infectivity but has no effect on viral replication.

Figure 5:
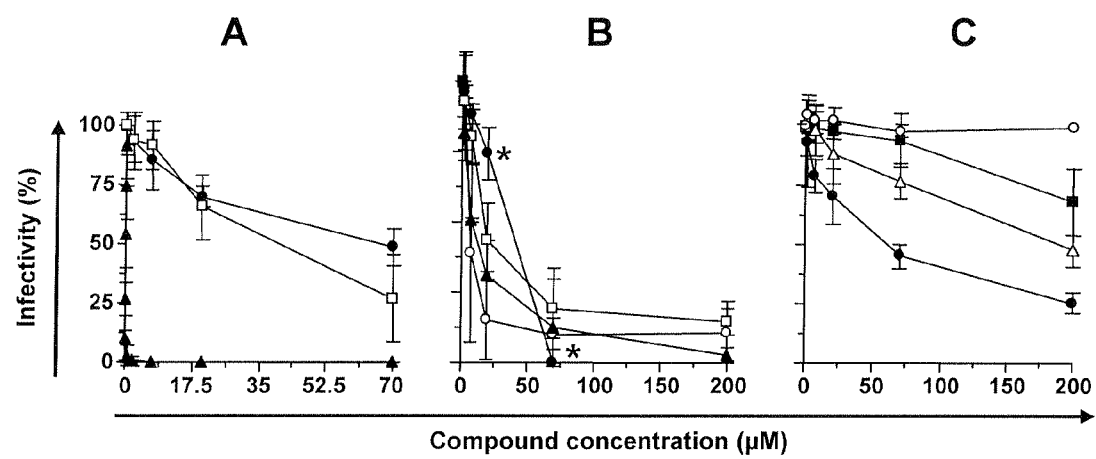
FIG. 5 are line graphs showing HSV-1 infectivity plotted against concentration of the different amphipathic nucleoside derivatives.

IV. Structure-Activity Relationship (SAR) Studies of the Antiviral Amphipathic Nucleoside Derivatives Structure-activity relationship (SAR) studies were applied to test the effects of amphipathicity, rigidity, and molecular shape on infectivity of herpes simplex virus type 1 (HSV-1), a good model in antiviral drug discovery. FIG. 4 shows the chemical structures and orthogonal views of the three-dimensional structures of the test compounds. FIG. 5 shows line graphs of HSV-1 infectivity plotted against concentration of the different amphipathic nucleoside derivatives. HSV-1 KOS (200 PFU) were incubated with 0, 2, 7, 20, 70 or 200 µM dUY2 (black circles), dUY3 (white squares), dUY11 (black triangles) (A); dUY4 (black triangles), dUY5 (black circles), dUY6 (white squares), dUY8 (white circles) (B); or dUY7 (white circles), dUY9 (black squares), dUY1 (white triangles), aUY1 (black circles) (C) for 5 minutes at 37° C. Vero cells were then infected for 1 hour with the so-pretreated virions, washed and overlaid with medium supplemented with 5% FBS and 2% MC. The maximum value in the x-axis scale is 70 µM for (A) and 200 µM for (B) and (C). The percent infectivity for virions pretreated with dUY11 (C) is too close to the axes in this scale and it is thus not clearly visible. Error bars represent ranges of three or more experiments. Among inverted cone shape compounds with rigid planar hydrophobic moieties, decreases in hydrophobic moiety sizes decreased activity (dUY11 versus dUY2, dUY3; FIG. 5A). Activities of compounds with similarly sized hydrophobic derivatives were reduced by rotational flexibility or non-planarity in the hydrophobic moiety (dUY11 versus dUY4, dUY5, dUY6, dUY8; FIGS. 5 A,B), which reduced the inverted cone shape. Activity was disrupted by two polar groups in the linker or core hydrophobic moieties (dUY7, dUY9; FIG. 5 C), which would prevent proper positioning of the inverted cone into the membrane. Activity was also inhibited by one polar group, but was rescued by increasing polarity of the hydrophilic moiety (aUY1 versus dUY1; FIG. 5 C). Amphipathicity and inverted cone shape as well as planarity and rigidity of the hydrophobic moiety are important for antiviral activity.

V. Characterization of dUY11 Activities on HSV Infectivity

Figure 6:
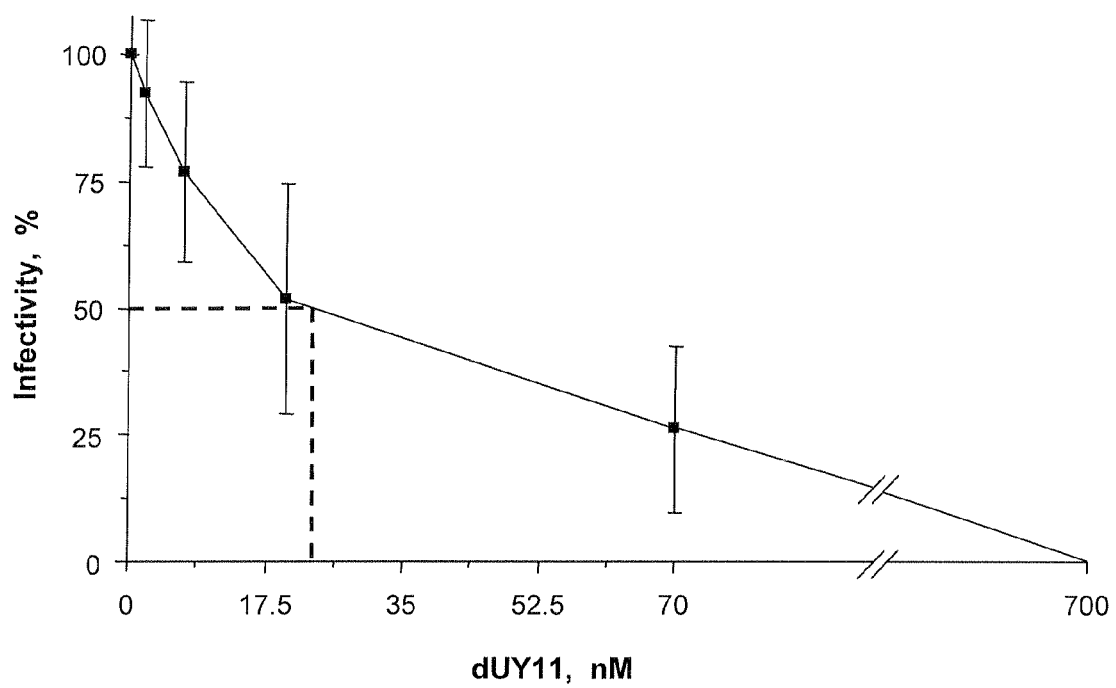
FIG. 6 is a line graph showing HSV-1 infectivity plotted against dUY11 concentration, where the $IC_{50}$ is 20 nM.

FIG. 6 is a line graph showing HSV-1 infectivity plotted against dUY11 concentration. HSV-1 KOS (200 PFU) was incubated with 0, 2, 7, 20, 70, 200 or 700 nM dUY11 for 5 minutes at 37° C. Vero cells were then infected with the so-pretreated virions for 1 hour, washed and overlaid with medium supplemented with 5% FBS and 2% MC. The concentration of dUY11, which inhibited 50% of HSV-1 infectivity ($IC_{50}$), was calculated graphically to be 20 nM. Error bars represent ranges of ten experiments. dUY11 was active in the low to medium nanomolar range, displaying an $IC_{50}$ of 20 nM.

Figure 7:
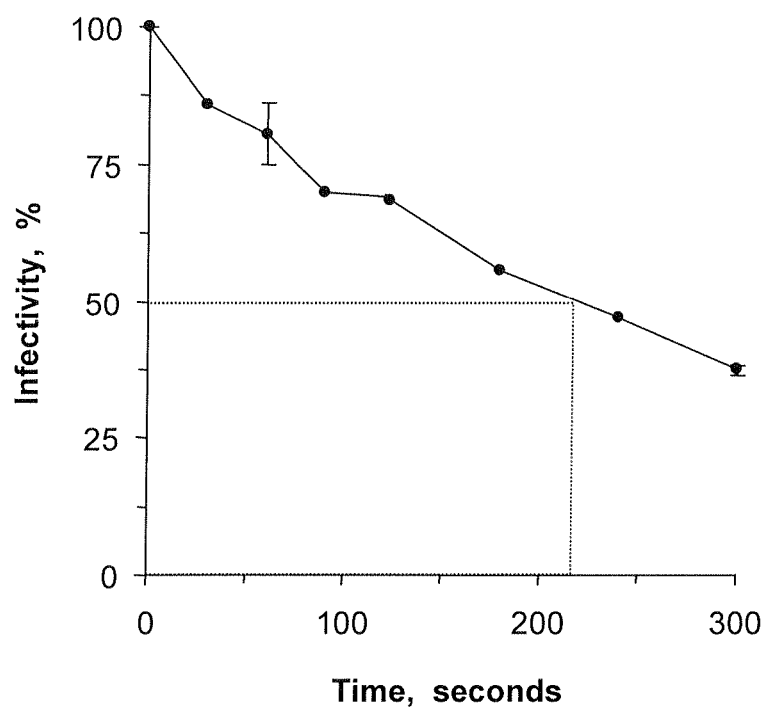
FIG. 7 is a line graph showing HSV-1 infectivity plotted against treatment time.

FIG. 7 is a line graph showing HSV-1 infectivity plotted against treatment time. HSV-1 KOS (200 PFU) was incubated with 20 nM ($IC_{50}$) dUY11 at 37° C. for 0, 30, 60, 90, 120, 180, 240 or 300 seconds. Vero cells were then infected with the so-pretreated virions for 1 hour, washed and overlaid with medium supplemented with 5% FBS and 2% MC. $IC_{50}$ dUY11 inhibits HSV-1 infectivity by 50% in 220 seconds (FIG. 7). Error bars represent the range of two experiments, but are not visible in this scale for most data points.

Figure 8:
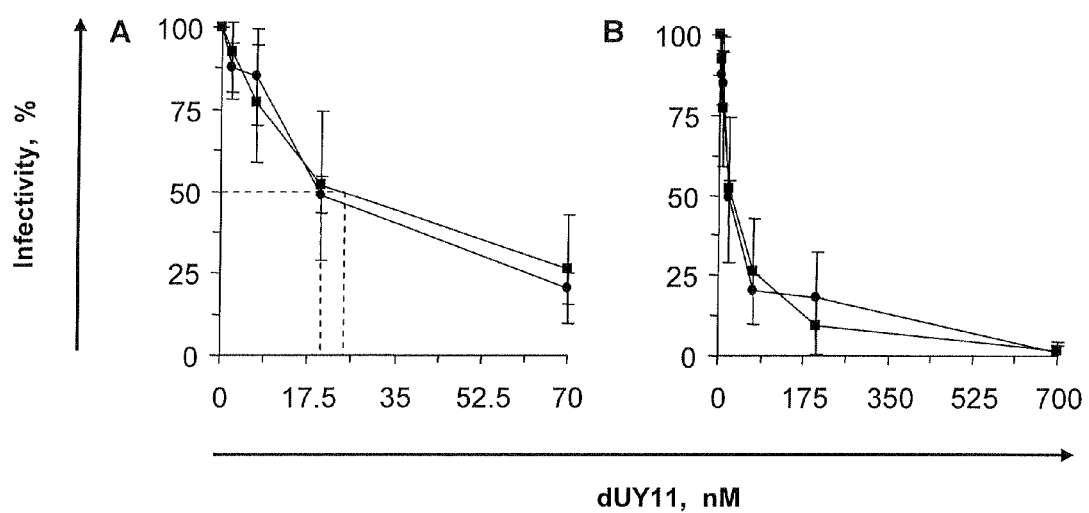
FIG. 8 is a line graph showing HSV-1 infectivity plotted against dUY11 concentration, where inhibition is independent of cell type.

FIG. 8 is a line graph showing HSV-1 infectivity plotted against concentration of dUY11. HSV-1 KOS (200 PFU) was incubated with 0, 2, 7, 20, 70, 200 or 700 nM dUY11 for 5 minutes at 37° C. Human Foreskin Fibroblasts (HFF) (●) or Vero cells (■) were then infected for 1 hour with the so-pretreated HSV-1 virions, washed and overlaid with medium supplemented with 5% FBS and 2% MC. $IC_{50}$ was calculated graphically to be 25 nM in Vero cells and 20 nM in HFF (A). Infectivity in both cell lines was fully inhibited when virions were pretreated with 700 nM dUY11 (B). Error bars represent ranges of three or more experiments. As expected, dUY11 treated virions were equally non-infectious for Vero cells or Human Foreskin Fibroblasts.

Although dUY11 is a potent and non-cytotoxic compound that protects mice from genital infection (see next sections), two other nucleoside-based compounds were synthesized and evaluated. The modified compounds are named ddUY11 and aUY11 (see Section I). The compounds were tested on infections of cultured cells. Both aUY11 and ddUY11 were approximately as potent as dUY11 (Table 1), and neither were cytotoxic.

TABLE 1

| $IC_{50}$ of aUY11, dUY11 and ddUY11 on infectivity of HSV-1 on Vero cells. | |
|---|---|
| Compound | IC50 (µM) |
| aUY11 | 0.075 |
| dUY11 | 0.050 |
| ddUY11 | 0.045 |

Figure 9:
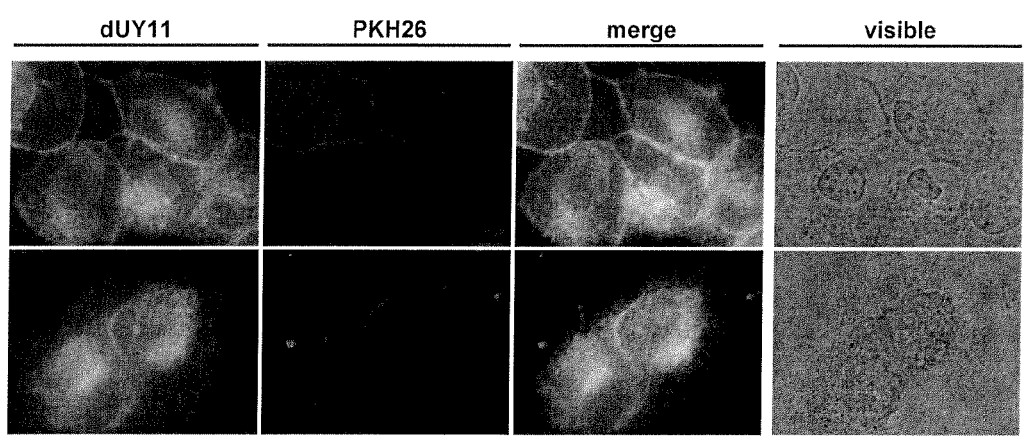
FIG. 9 shows mock-infected cells treated with dUY11 and counterstained with a membrane dye (PKH26).

VI. dUY11 has a Safety Index Larger than 7,500 and has No Major Cytostatic Effects Two series of experiments revealed that dUY11 has no cytotoxic or cytostatic effects. In the first series, fresh media supplemented with dUY11 had been replaced only at 30 hours during a total treatment of 72 hours. However, it was later discovered that dUY11 localizes to the plasma membrane (FIG. 9). The number of dUY11 molecules per plasma membrane would thus decrease by half after each cell duplication cycle. The cytotoxicity analyses were therefore repeated but adding fresh dUY11-containing media every 24 hours (which is approximately the doubling time for these cells) for a total exposure of 72 hours.

Figure 10:
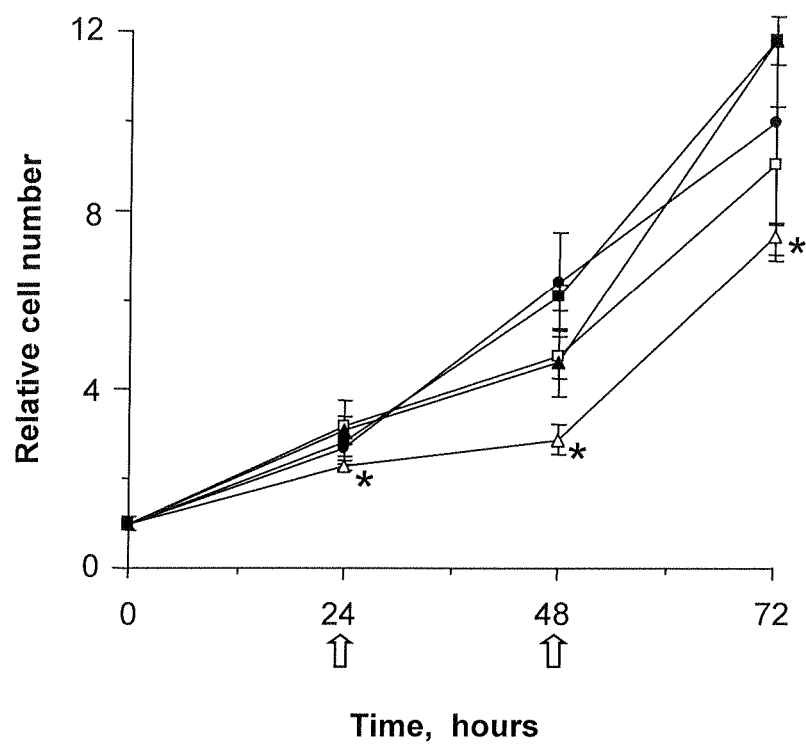
FIG. 10 is a line graph showing relative cells numbers plotted against time of exposure to dUY11, where dUY11 has no major cytotoxic or cytostatic effects.

FIG. 10 is a line graph showing relative cell numbers plotted against time of exposure to dUY11. Vero cells were mock infected for 1 hour, washed, and overlaid with media containing 0 (■), 7 (▲), 20 (●), 70 (□) or 150 (Δ) µM dUY11. 150 µM is not stable in medium for long periods. Media was replaced with fresh media supplemented with 0, 7, 20, 70 or 150 µM of dUY11 every 24 hours (indicated by the upward block arrows). Viable and non-viable cells were counted by trypan blue exclusion at 24, 48 and 72 hours. Non-viable cells accounted for less than 4% of total cells for all samples at all times. Error bars represent ranges of duplicate samples from one experiment, except for (*), where they represent ranges of duplicate counts of one sample from one experiment. dUY11 was not cytotoxic and only mildly cytostatic, even at concentrations 7.500-fold above its $IC_{50}$. The safety index (SI) is thus larger than 7,500 but the value could not be calculated because 50% cytotoxicity could not be reached at any concentration at which dUY11 was homogeneously dispersed in media (up to 70,000 nM), or even at higher concentrations (150,000 nM).

VII. The Amphipathic Nucleoside Derivatives Inhibit Viral Entry, but Not Binding.

Figure 11:
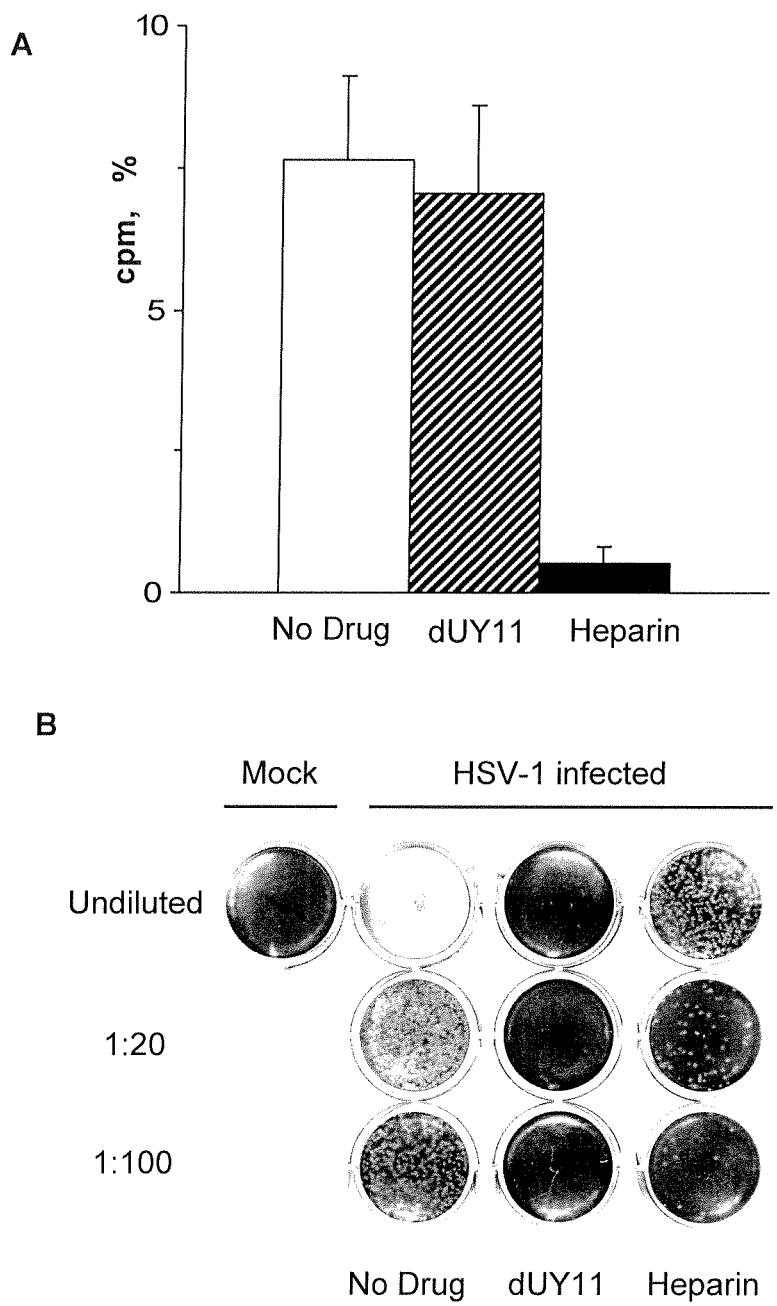
FIG. 11 is a bar graph and photographic images showing HSV-1 binding (A) and infectivity (B), where dUY11 does not inhibit HSV-1 binding.
Figure 12:
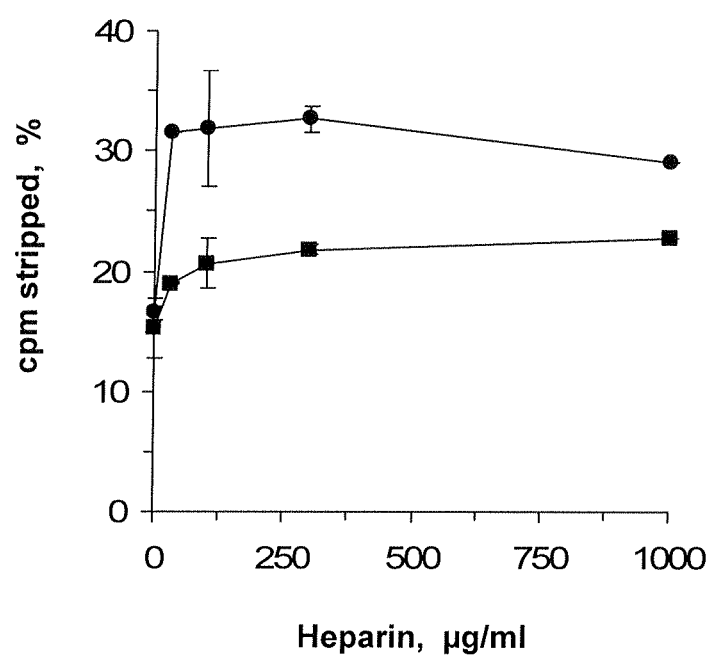
FIG. 12 is a line graph showing competition of HSV-1 binding to cells by increasing the concentration of heparin, where dUY11 does not block high-affinity binding by HSV-1 virions.

Infectivity was inhibited by pre-treating HSV-1 virions with the amphipathic nucleoside derivatives before infection. These nucleosides may thus inhibit HSV-1 infectivity by, for example, preventing virion binding to cells. Alternatively, they may disrupt extracellular virions (i.e. have virucidal activities). Lysed virions do not bind to cells. The binding of HSV-1 virions pre-treated with dUY11 was assessed. FIG. 11 is a bar graph and photographic images showing HSV-1 binding (A) and infectivity (B). In parallel studies, [35]S-Methionine radiolabeled (approximately $4 \times 10^5$ cpm in $2.5 \times 10^5$ PFU) (A) or non-radiolabeled HSV-1 KOS (B) were pre-treated with no drug (white bar), 7 μM dUY11 (striped bar), or 100 μg/ml heparin (black bar) for 5 minutes at 37° C. The samples were then cooled on ice. Inocula were diluted (1:20, 1:100) in ice-cold serum-free media supplemented with no drug, 7 μM dUY11, or 100 μg/ml heparin. Vero cells were infected with the so-pretreated virions at 4° C. for 1 hour, washed three times with ice-cold serum-free medium and lysed. Bound virions were quantified by liquid scintillation. Error bars represent ranges of three experiments (A). Based on these results, 7 μM dUY11 did abrogate infectivity (FIG. 11B) but did not inhibit virion binding (FIG. 11A).

dUY11 was next evaluated for its ability to affect high-affinity binding. FIG. 12 is a line graph showing competition of HSV-1 binding to cells by increasing concentration of heparin. [35]S-Methionine radiolabeled HSV-1 (approximately $3.5 \times 10^5$ cpm in $2.5 \times 10^5$ PFU) was pretreated with 7 μM dUY11 (■) or with no drug (●) for 5 minutes at 37° C. Inocula were cooled on ice, and then diluted (1:10) in ice-cold serum-free media with or without 7 μM dUY11. Following 15 minute adsorption onto Vero cells, unbound virions were washed away. Bound virions were then further washed for 1 hour with media supplemented with 0 to 1,000 μg/ml heparin to remove those virions bound by only low-affinity binding. Virions stripped away by these washes were then quantified by liquid scintillation. Error bars represent ranges of two experiments. Heparin could not compete as efficiently with the binding of HSV-1 virions pre-treated with 7 μM dUY11 as with the untreated ones, indicating that the former were mostly attached by high-affinity binding (FIG. 12). Thus, dUY11 is not virucidal and does not block either low- or high-affinity binding. Therefore, the amphipathic nucleoside derivatives inhibit a step between high-affinity binding and viral DNA replication.

The effects of dUY11 on HSV-1 entry were investigated next. HSV entry can be assessed by several means, including the evaluation of VP16 entry into the infected cell. VP16 is the only HSV virion protein required for activation of HSV immediate-early (IE) gene transcription. Therefore, VP16 entry can be assessed in cells containing a red fluorescence protein (RFP) reporter gene recombined into their cellular genomes under the control of an HSV-1 IE promoter. Expression of RFP after infection indicates that VP16 has reached the nucleus. Therefore, it also indicates that HSV has entered the cell.

Figure 13:
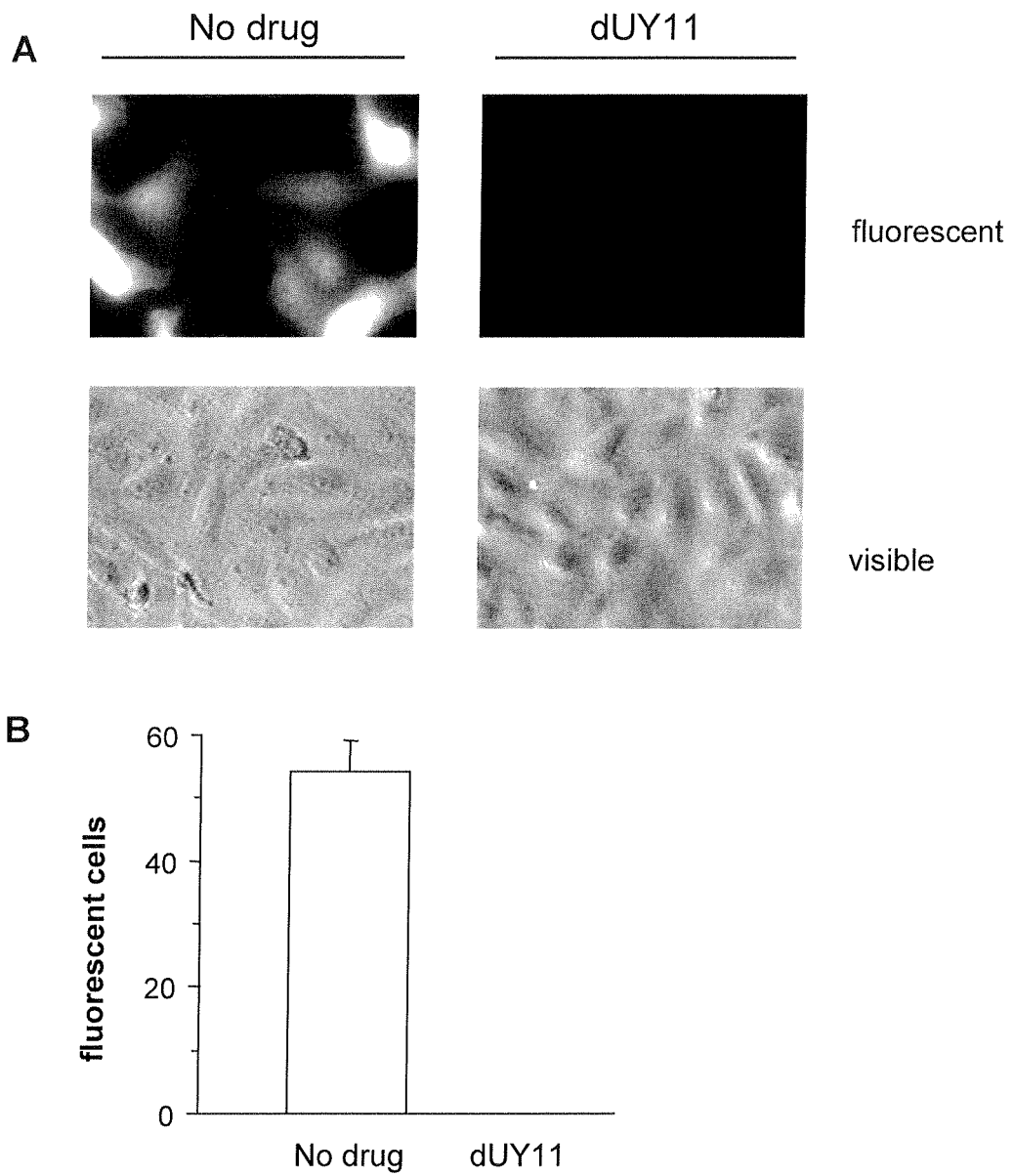
FIG. 13 shows representative pictures (A) and quantification (B) of red fluorescence protein expression in Vero cells containing a red fluorescence protein (RFP) reporter gene recombined into their cellular genomes under the control of the HSV-1 ICP0 IE promoter, where dUY11 inhibits HSV-1 entry.

FIG. 13 shows representative pictures (A) and quantification (B) of red fluorescence expression in Vero cells containing a red fluorescence protein (RFP) reporter gene recombined into their cellular genomes under the control of the HSV-1 ICP0 IE promoter. Cells were infected with HSV-1 KOS virions pretreated with DMSO vehicle (left panels) or 2 μM dUY11 (right panels). In FIG. 13A, cells were visualized at 24 hpi by fluorescence (top panels) or visible light (bottom panels). In FIG. 13B, quantification of fluorescent cells infected with UV-inactivated HSV-1 KOS virions pretreated with no drug or dUY11 (counts from two microscopic fields with similar cell densities from one experiment, representative of 7 experiments).

Cells expressing RFP under the control of an HSV-1 IE promoter and infected with HSV-1 virions pre-treated with 2 μM of dUY11 (3.5-fold lower than the concentrations that failed to inhibit binding), produced no detectable fluorescence (FIG. 13). Therefore, dUY11 inhibits a step after high-affinity binding but prior to virion entry. The only known step in between them is the fusion between the viral envelope and the cellular membrane.

VIII. The Amphipathic Nucleoside Derivatives Inhibit Infectivity of Several Otherwise Unrelated Enveloped Viruses To test whether the target of dUY11 is conserved among viruses that have somewhat conserved glycoproteins, we tested dUY11 activity on two strains of HSV type 2 (HSV-2). The first is a clinical isolate and the other a laboratory-adapted strain (strains 186 and 333, respectively). To test whether the target of dUY11 is conserved in only distantly related enveloped viruses, the activity of dUY11 was tested on vesicular stomatitis virus (VSV) and Sindbis (SIN). VSV and SIN are RNA viruses with no glycoprotein known to be conserved with HSV-1 or -2. The glycoproteins of VSV and SIN also recognize different receptors than those in HSV-1 or -2. The G-protein of VSV recognizes and binds to a specific lipid, phosphatidylserine, whereas the SIN glycoproteins bind to the high-affinity laminin receptor, a ubiquitous surface protein. In contrast to HSV-1 or -2, VSV and SIN are internalized by fusing with endosomal membranes following low-pH induced conformational changes in their fusion glycoproteins. These conformational changes expose the fusion peptides, which are then inserted into the target membrane and trigger fusion between the viral envelope membrane and the cellular membrane.

Figure 14:
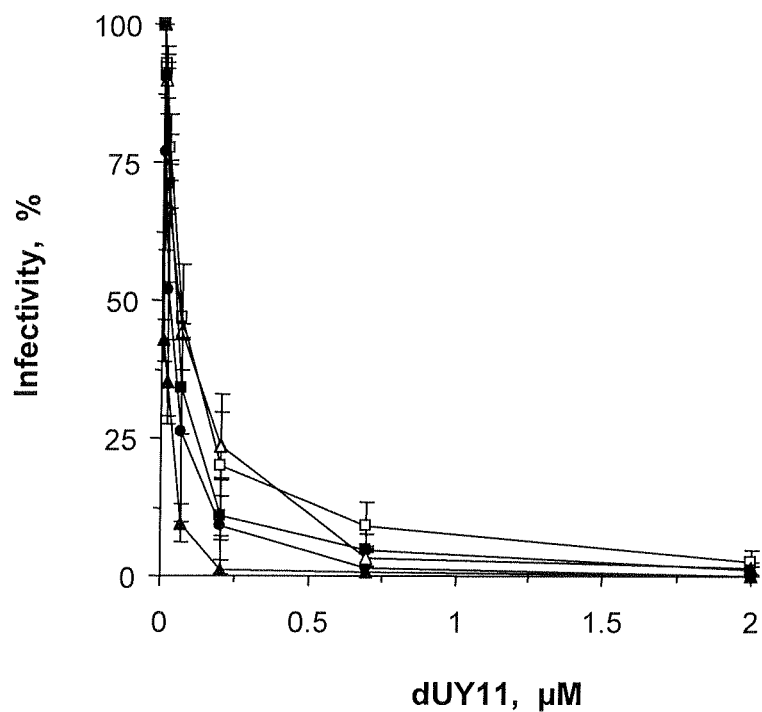
FIG. 14 is a line graph showing infectivity of HSV-1 strain KOS, HSV-2 strain 186, HSV-2 strain 333, VSV or Sindbis virus plotted against concentration of dUY11, where dUY11 inhibits infectivity of HSV-1, HSV-2, VSV, and Sindbis virus.

FIG. 14 is a line graph showing infectivity of HSV-1 strain KOS (●), HSV-2 strain 186 (■), HSV-2 strain 333 (□), VSV (▲) or SIN virus (Δ) plotted against concentration of dUY11. Virions (200 PFU) were incubated with 0, 0.007, 0.02, 0.07, 0.2, 0.7 or 2 μM dUY11 for 5 minutes at 37° C. Vero cells were then infected for 1 hour with the so-pretreated virions, washed and overlaid with medium supplemented with 5% FBS and 2% MC. The $IC_{50}$ was calculated graphically to be 6 nM for VSV, 24 nM for HSV-1, 49 nM for HSV-2 strain 186, 58 nM for SIN and 65 nM for HSV-2 strain 333. Error bars represent ranges of two or more experiments. dUY11 inhibited infectivity of both strains of HSV-2 with similar $IC_{50}$ as toward HSV-1 (FIG. 14), indicating that the target of dUY11 is conserved among viruses with conserved glycoproteins and envelope lipid composition. It also inhibited with similar $IC_{50}$ distantly related enveloped viruses, indicating that the target of dUY11 is also conserved among viruses with non-conserved envelope proteins. Therefore, dUY11 inhibits a step of viral fusion that is conserved among otherwise unrelated enveloped viruses. Because dUY11 prevents entry of unrelated enveloped viruses but does not block high-affinity binding, it is proposed that the target of dUY11 is the fusion between the lipid membrane bilayers of the envelope and cell.

IX. The Main Target of the Amphipathic Nucleoside Derivatives is the Viral Envelope, Not the Cellular Membrane Viral internalization requires fusion between two lipid bilayer membranes, the viral envelope and the cell membrane. Viral infectivity was inhibited when virions were pre-treated with dUY11, thus indicating that the viral envelope is a target. However, the cell membrane may also be a target. Under this scenario, dUY11-pre-treated virions would deliver the drug to the target sites in the plasma membrane. Then, pre-treating cells should inhibit infection more efficiently than pre-treating virions.

Figure 15:
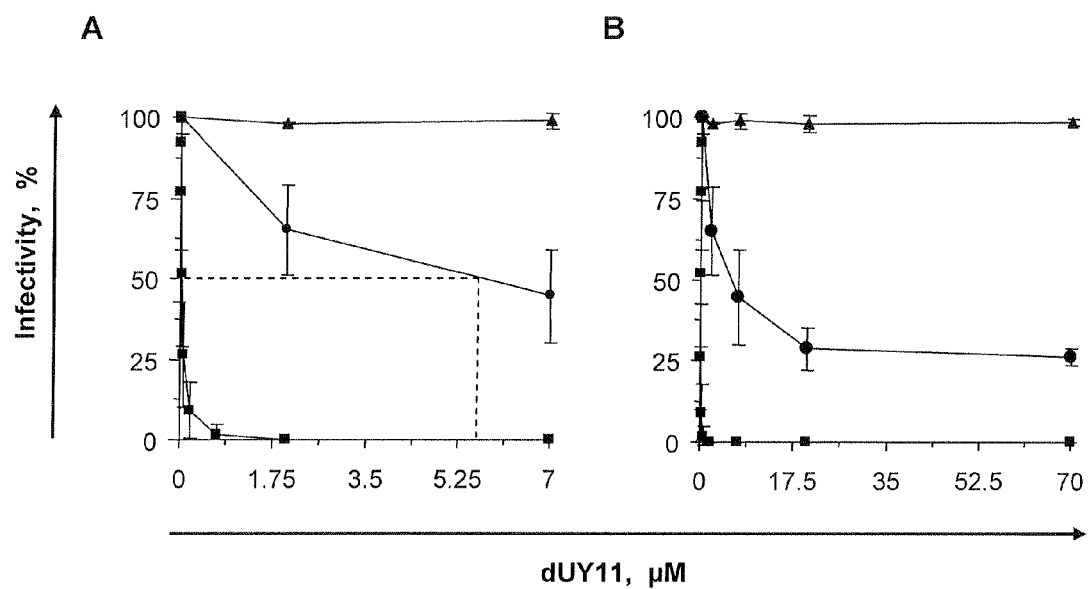
FIG. 15 are line graphs showing HSV-1 KOS infectivity plotted against dUY11 concentrations used to pre-treat virions or cells, or to treat cells only after infection, where dUY11 only inhibits HSV-1 infectivity totally if it is used to pre-treat virions.

Tests were performed to determine whether dUY11 preferentially targets the viral envelope or the cell membrane. FIG. 15 are line graphs showing HSV-1 KOS infectivity plotted against dUY11 concentration. HSV-1 KOS (200 PFU) were incubated with 0, 0.002, 0.007, 0.02, 0.07, 0.2, 0.7, 2, 7, 20 or 70 µM dUY11 for 5 minutes at 37° C. Vero cells were then infected with so-pretreated virions for 1 hour, washed and overlaid with medium supplemented with 5% FBS and 2% MC (■). Alternatively, untreated inocula were used to infect untreated Vero cells (▲) or Vero cells pretreated at 37° C. for up to 60 minutes with 0, 2, 7, 20 or 70 µM dUY11 (●). Non-pretreated infected cells were then overlayed with medium supplemented with 5% FBS and 2% MC supplemented with 0, 2, 7, 20 or 70 µM dUY11. $IC_{50}$ was calculated graphically to be 20 nM for virion pretreatment (not visible in these scales) and 5.4 µM for cell pretreatment (A). Maximum inhibition is 100% for virion pretreatment or 75% for cell pretreatment (B). The maximum value in the x-axis scale is 7 µM for (A) and 70 µM for (B). Error bars represent ranges of three or more experiments.

Viral infectivity was fully inhibited only when virions were pre-treated prior to infection ($IC_{50}$, 20 nM—FIG. 15). In contrast, pre-treatment of cells reduced HSV-1 infectivity, but only up to 75% and at 270-fold higher concentrations ($IC_{50}$, 5.4 µM). Consistent with the results presented in FIG. 3, treatment of cells with dUY11 after infection with untreated virions had no effect on HSV-1 replication. These results indicate that the membrane primarily targeted by the amphipathic nucleoside derivatives is the viral envelope and further proves that these compounds do not inhibit viral replication.

Figure 16:
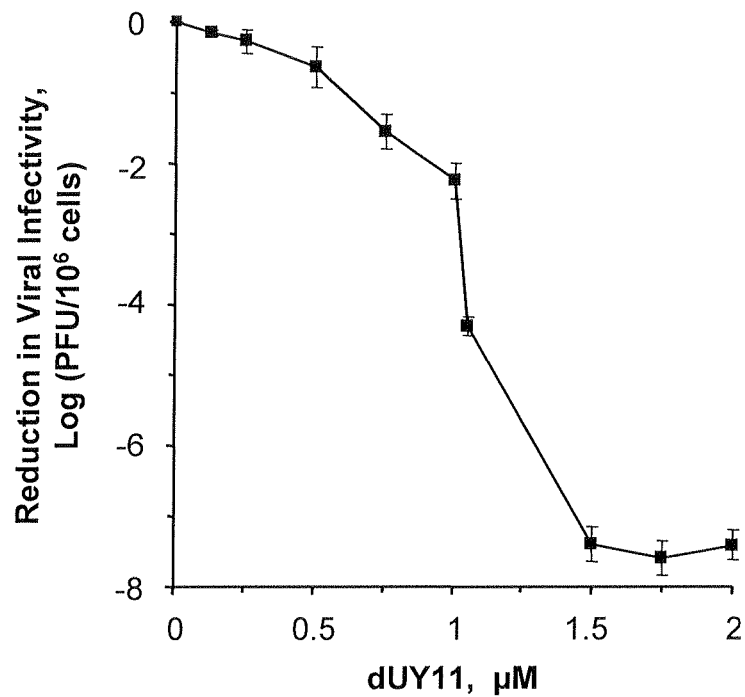
FIG. 16 is a line graph showing the reduction in infectivity of virions produced by cells treated with amphipathic nucleoside derivatives for 24 or only 1 hours and plotted against drug concentration, where dUY11 inhibits the infectivity of progeny virions.
Figure 16:
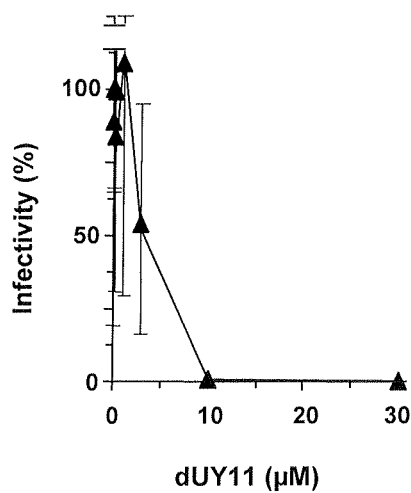

X. Amphipathic Nucleoside Derivatives Inhibit Infectivity of Virions Produced by Treated Cells If the amphipathic compounds could insert themselves into cellular, as well as viral membranes, then they could also inhibit the infectivity of progeny virions produced by treated cells. FIG. 9 shows mock-infected cells treated with dUY11 and counterstained with a membrane dye (PKH26). dUY11 is indeed distributed to plasma and intracellular membranes, although absent from filopodia, which indicates that dUY11 does not block membrane trafficking. Virions produced by cells infected and treated with said compounds after infection should therefore not be as infectious as virions produced by untreated cells. FIG. 16A is a line graph showing the reduction in infectivity of virions produced by cells treated with amphipathic nucleoside derivatives for 24 hours and plotted against drug concentration. Vero cells were infected with HSV-1 KOS at a multiplicity of infection (MOI) of 3 PFU/cell. After removing the viral inoculum, infected cells treated with 0, 0.125, 0.25, 0.5, 0.75, 1, 1.05, 1.5, 1.75 or 2 µM of dUY11. Cells were harvested at 24 hpi and viral infectivity was evaluated by standard plaque assays. Error bars represent ranges of 3 or more experiments. The virions produced in the presence of dUY11 were 8 orders of magnitude less infectious than those produced by untreated cells (FIG. 16A). The experiments were then repeated, but limiting the exposure of the infected cells to dUY11 to only 1 hour, immediately after removing the viral inoculum (FIG. 16B). Cells were then infected with HSV-1 and dUY11 was added to the infected cells for only 1 h, before envelope glycoproteins are expressed. Infected cells were then incubated without drug for 22 h, then the infectivity of the progeny virions was assessed. Virions budded from dUY11-treated cells were 6 orders of magnitude less infectious than those budded from untreated cells (FIG. 16B; $IC_{50}$, 3.9 µM). Therefore, dUY11 interacts with pre-existing cellular factors that are incorporated into virions, such as membrane lipids.

The effects of dUY11 on the infectivity of virions produced by treated cells was independent of whether the infecting virus was susceptible (i.e., wild-type) or resistant to conventional antiviral drugs. dUY11 had equally important inhibitory effects on the infectivity of virions produced by cells infected with wild-type, acyclovir- or phosphonoacetic acid-resistant HSV-1 strains resistant (strains thymidine kinase—TK—deleted or $PAA^{r5}$, respectively).

Figure 17:
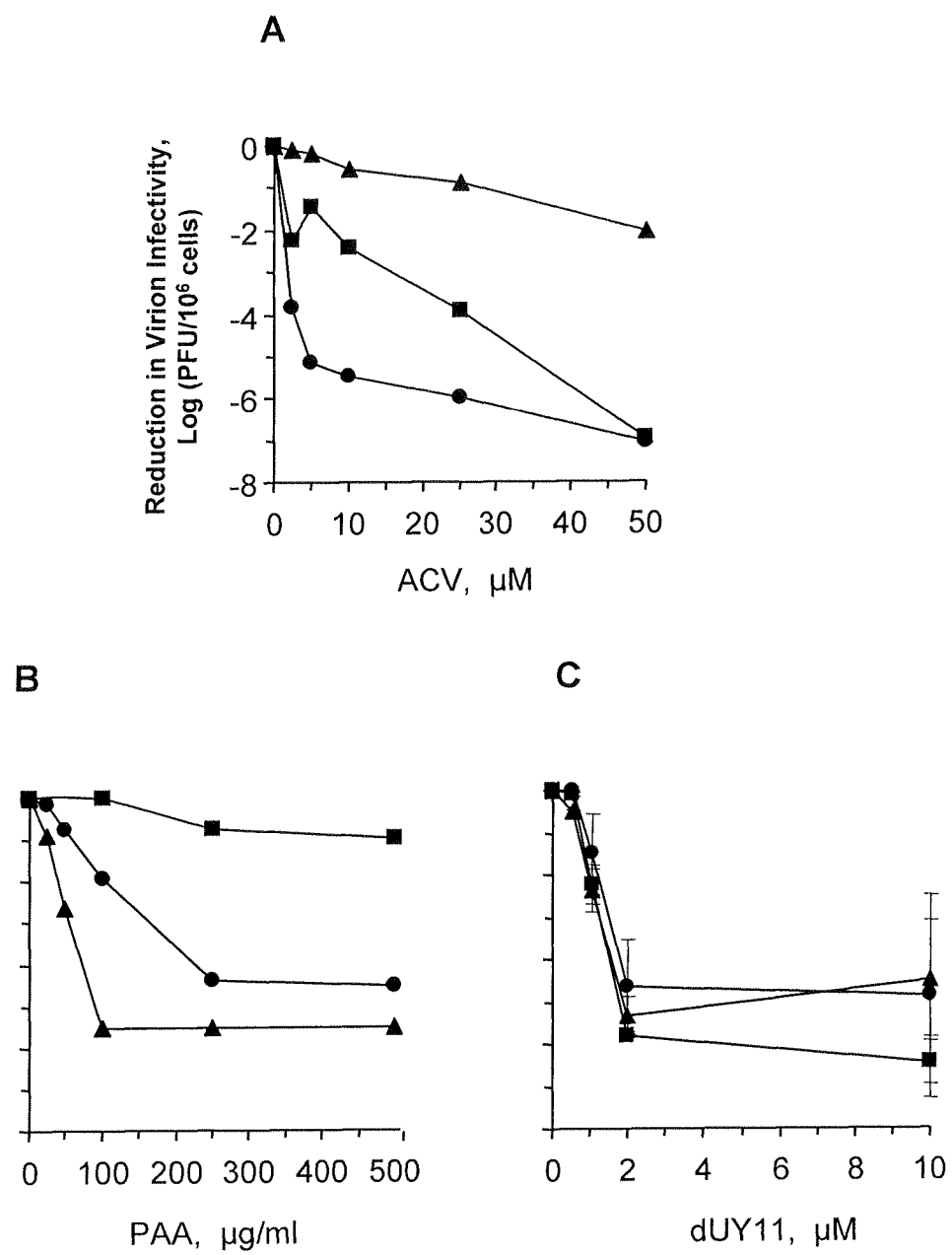
FIG. 17 are line graphs showing the reduction in viral infectivity (or viral titers) of virions produced by cells treated with different drugs and plotted against the concentration of ACV, PAA or dUY11, where dUY11 inhibits the infectivity of drug-resistant mutant virions.

FIG. 17 are line graphs showing the reduction in viral infectivity (or viral titers) of virions produced by cells treated with different drugs and plotted against the concentration of ACV, PAA or dUY11. Vero cells were infected with 3 PFU/cell of WT (●), ACV-(▲) or PAA-resistant (■) HSV-1 for 1 h, washed, and overlaid with medium containing (A) 0, 2.5, 5, 10, 25 or 50 µM ACV, (B) 0, 25, 50, 100, 250 or 500 µg/ml PAA, or (C) 0, 0.5, 1.05, 2 or 10 µM dUY11. Cells were harvested 24 h later and viral infectivity (or viral titers) was evaluated by standard plaque assays. Reduction of viral infectivity (or viral titers) was calculated by dividing the infectivity of virions produced by cells treated with the different drugs by the infectivity of virions produced by untreated cells. Error bars represent ranges of two experiments.

These experiments further prove that the amphipathic nucleoside derivatives do not target the HSV-1 TK or the pyrophosphate binding site of the viral DNA polymerase (the target of PAA) as most other nucleoside derivatives do.

XI. In Vivo Analysis of Amphipathic Nucleoside Derivatives

Figure 18:
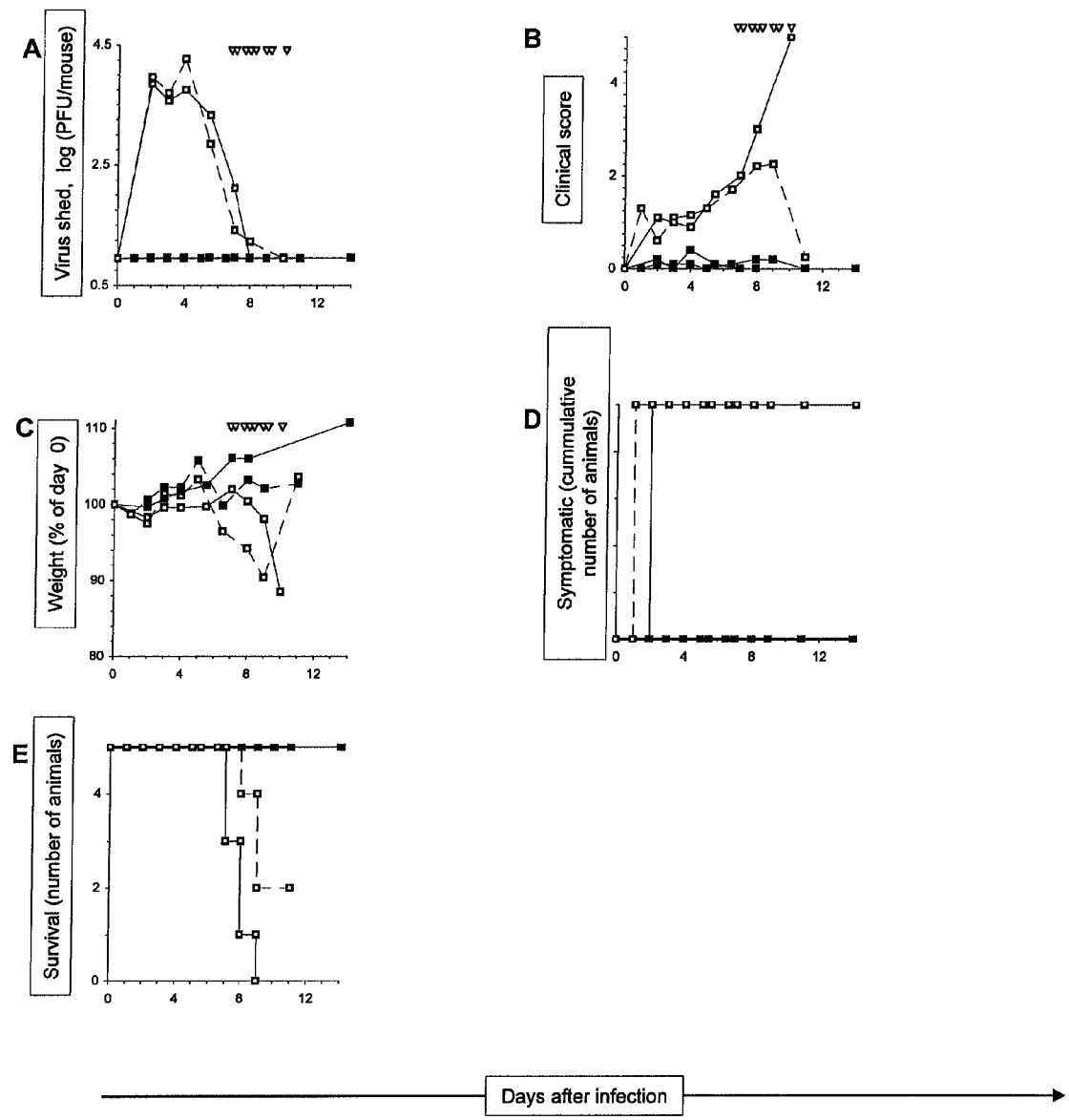
FIG. 18 are graphs showing the ability of dUY11 to protect mice in vivo from vaginal infection with HSV-2, where dUY11 exposed virions are non-infectious to mice.
Figure 19:
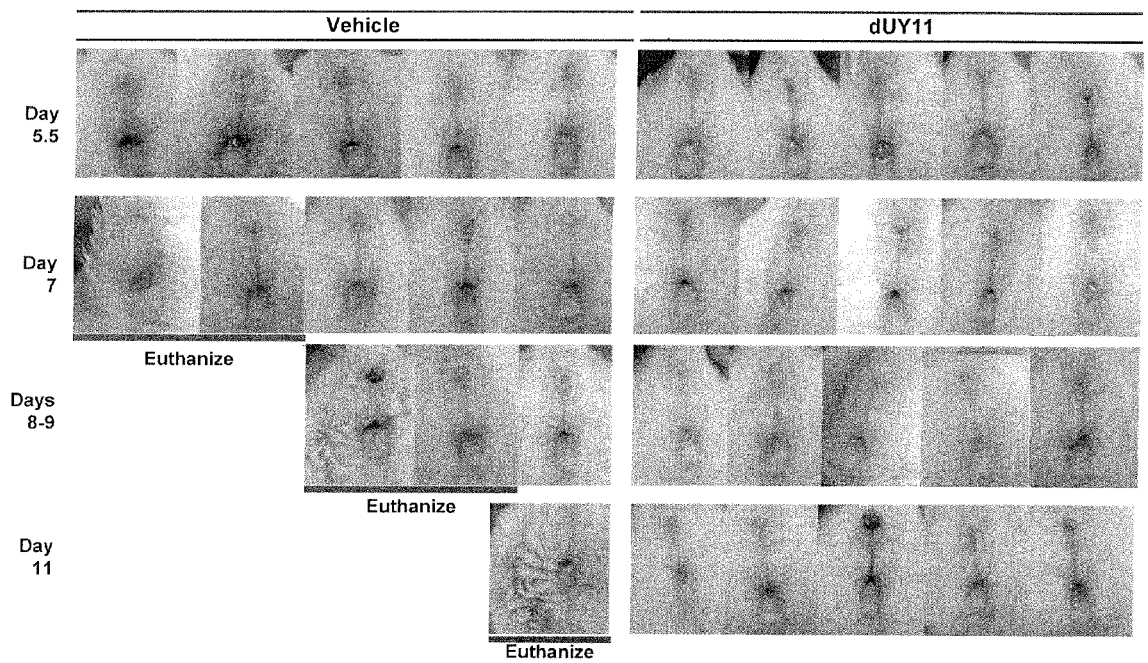
FIG. 19 are photographs of the vaginal region, perineal region, and anus of mice infected with HSV-2 exposed to dUY11, where dUY11 exposed virions are non-infectious to mice.
Figure 19:
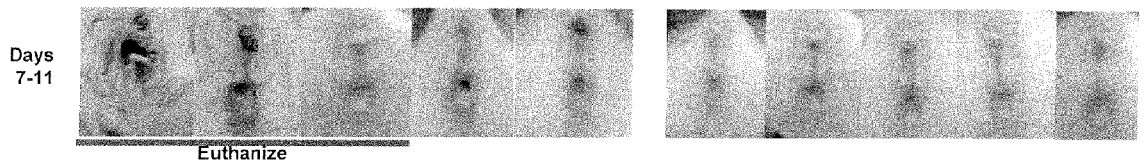

In order to determine whether an amphipathic nucleoside derivative described herein inhibited viral transmission, a model vaginal infection with a sexually transmitted virus, HSV-2, was used. Groups of five mice were vaginally infected with $10^3$ or $3 \times 10^3$ infectious HSV-2 virions exposed to 70 µM dUY11 or vehicle (FIG. 18A-E and FIG. 19A-B). FIGS. 18A-E shows viral shedding, average clinical scores or relative weights, cumulative number of symptomatic and dead mice infected with 1,000 (dashed line) or 3,000 (solid line) infectious HSV-2 virions exposed to vehicle (white squares) or dUY11 (black squares). FIGS. 19A-B shows photographs of the vaginal, perineal region and anus of all infected mice. FIG. 19A shows mice infected with 3,000 infectious HSV-2 virions exposed to vehicle (left panels) or dUY11 (right panels). FIG. 19B shows mice infected with 1,000 infectious HSV-2 virions exposed to vehicle (left panels) or dUY11 (right panels). All mice infected with virions exposed to vehicle shed ~$10^4$ infectious virions between days 2 and 4 post infection, and lower levels to day 8, and displayed obvious clinical signs of infection (FIG. 18A-D). All five mice infected with $3 \times 10^3$ infectious virions, and three of the mice infected with $10^3$, had to be euthanized between days 7 and 9 due to advanced illness (FIGS. 18E and 19A-B). None of the ten mice infected with either $10^3$ or $3 \times 10^3$ virions exposed to dUY11 shed detectable infectious virus or showed clinical signs of infection. Therefore, dUY11 protects from vaginal infection with HSV-2.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed is:

1. A compound having the formula IIIA

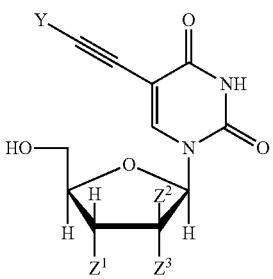

IIIA wherein $Z^1$ and $Z^2$ are OH, $Z^3$ is H, and Y is a substituted or unsubstituted fused aromatic group comprising three or more aryl rings, or the pharmaceutically-acceptable salt or ester thereof.

2. The compound of claim 1, wherein the fused aromatic group has the structure

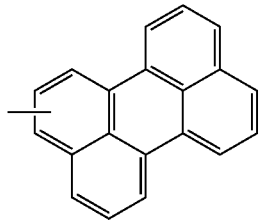

wherein the fused aromatic group is substituted or unsubstituted.

3. The compound of claim 1, wherein Y is a fused aromatic group has the structure

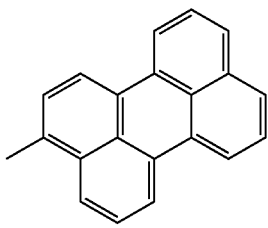 [SMILES: Cc1ccc2c3cccc4cccc(c5cccc1c52)c43]

wherein the fused aromatic group is substituted or unsubstituted.

4. A pharmaceutical composition comprising the compound of claim 1 and a pharmaceutically-acceptable carrier.

5. The composition of claim 4, wherein the pharmaceutical composition is a topical composition.

* * * * *